United States Patent
Pershadsingh et al.

(10) Patent No.: US 6,204,288 B1
(45) Date of Patent: Mar. 20, 2001

(54) 1,2-DITHIOLANE DERIVATIVES

(75) Inventors: Harrihar A. Pershadsingh, Bakersfield, CA (US); Mitchell A. Avery, Oxford, MS (US)

(73) Assignee: The University of Mississippi, University, MS (US)

( * ) Notice: Subject to any disclaimer, the term of this patent is extended or adjusted under 35 U.S.C. 154(b) by 0 days.

(21) Appl. No.: 09/497,324

(22) Filed: Feb. 3, 2000

Related U.S. Application Data

(62) Division of application No. 09/264,370, filed on Mar. 8, 1999.

(51) Int. Cl.[7] .................. C07C 323/59; A61K 31/92
(52) U.S. Cl. .................. 514/440; 514/538; 514/562; 560/9; 562/426; 549/39
(58) Field of Search ............... 549/39; 560/9; 562/426; 514/440, 538, 562

(56) References Cited

U.S. PATENT DOCUMENTS

| | | | |
|---|---|---|---|
| 4,287,200 | 9/1981 | Kawamatsu et al. | 424/270 |
| 4,572,912 | 2/1986 | Yoshioka et al. | 514/369 |
| 4,918,091 | 4/1990 | Cantello et al. | 514/369 |
| 5,338,855 | 8/1994 | Yoshioka et al. | 514/369 |
| 5,594,015 | 1/1997 | Kurtz et al. | 514/369 |
| 5,661,168 | 8/1997 | Panetta et al. | 514/369 |
| 6,013,663 | 1/2000 | Fujita et al. | 514/440 |

FOREIGN PATENT DOCUMENTS

WO 97/31907   9/1997   (WO) .................. C07D/263/56

OTHER PUBLICATIONS

Schweizer, E., et al., "Reactions of Phosphorus Compounds. XIX. Reactions of 3–(o–Formylphenoxy)propyltriphenylphosphonium Bromide and 3–(p–Formylphenoxy)propyltriphenylphosphonium Bromide," *J. Org. Chem.*, 34(1):207–212 (1969).

Newman, et al., "Thiophenols from Phenols: 2–Naphthalenthiol," *Organic Synthesis*, 51:139–142 (1971).

Barry, "Properties That Influence Percutaneous Absoprtion," *Dermatological Formulations, Percutaneous Absorption*, 18:181–185 (1983).

Nate, H., et al., "Synthesis of 2–Phenylthiazolidine Derivatives as Cardiotonic Agents. II. 2–(Phenylpiperazinoalkoxyphenyl)thiazolidine–3–thiocarboxamides and the Corresponding Carboxamides," *Chem. Pharm. Bull.*, 35(6):2394–2411 (1987).

Calmes, M., et al., "Supramolecular Asymmetric Induction: A New Concept Applied to the Supported Enantioselective Synthesis of α–Amino Acids," *Tetrahedron*, 46(17):6021–6032 (1990).

Hulin B., et al., "Novel Thiazolidine–2,4–diones as Potent Euglycemic Agents", *J. Med. Chem.*, 35(10):1853–1864 (1992).

Suzuki, Y. J., et al., "An Antioxidant Activities of Dihydrolipoic Acid and its Structural Homologues", *Free Rad. Res. Comms.*, 18(2): 115–122 (1993).

Lehmann, J.M., et al., "An Antidiabetic Thiazolidnedione is a High Affinity Ligand for Peroxisome Proliferator–activated Receptor γ(PPAR γ)," *J. Biol. Chem.*, 270(22):12953–12956 (1995).

Wilson, T., et al., "The Structure—Activity Relationship Between Peroxisome Proliferator–Activated Receptor γ Agonism and the Anithyperglycemic Activity of Thiazolidinediones," *J. Med. Chem.*, 39(3): 665–668 (1996).

Perlmann & Evans, "Nuclear Receptors in Sicily: All in the Famiglia," *Cell*, 90:391–397(1997).

Tomkinson, Nicholas, C.O., et al., "Solid–phase synthesis of hybrid thiazolidinedione–fatty acid PPARγ ligands," *Bioorganic & Medicinal Chemistry Letters*, 7(19):2491–2496 (1997).

Nolte, Robert T., et al., "Ligand binding and co–activator assembly of the peroxisome proliferator–activated receptor–γ," *Nature*, 395:137–143 (Sep. 10, 1998).

Henke, Brad R., et al., "N–(2–benzoylphenyl)–l–tyrosine PPARγ agonists. 1. Discovery of a novel series of potent antihyperglycemic and antihyperlipidemic agents," *J. Med. Chem.*, 41:5020–5036 (1998).

Collins, Jon L., et al., "N–(2–benzoylphenyl)–1–tyrosine PPARγ agonists. 2. Structure—activity relationship and optimization of the phenyl alkyl ether moiety," *J. Med. Chem.*, 41:5037–5054 (1998).

Cobb, Jeff E., et al., "N–(2–benzoylphenyl)–1–tyrosine PPARγ agonists. 3. Structure—activity relationship and optimization of the N–aryl substituent," *J. Med. Chem.*, 41:5055–5069 (1998).

Berger, Joel, "Novel peroxisome proliferator–activiated receptor (PPAR)γ and PPARδ ligands produce distinct biological effects," *J. Biological Chemistry*, 274(10):6718–6725 (1999).

*Primary Examiner*—Robert Gerstl
(74) *Attorney, Agent, or Firm*—Townsend and Townsend and Crew

(57) ABSTRACT

This invention provides new thiazolindinedione derivatives also new arylacetic acid derivatives. These compounds are useful for the treatment of certain cardiovascular certain diseases, certain endocrine diseases, certain inflammatory diseases, certain neoplastic (malignant) and non-malignant proliferative diseases, certain neuro-psychiatric disorders, certain viral diseases, and diseases associated with these viral infections as discussed herein.

33 Claims, 13 Drawing Sheets

A

B

C

1,2-DITHIOLANE DERIVATIVES

This application is a Div. of Ser. No. 09/264,370 filed Mar. 8, 1999.

BACKGROUND OF THE INVENTION

Peroxisome proliferator-activated receptors (PPARs) are members of the nuclear receptor superfamily of ligand-activated transcription factors. Three subtypes of PPARs have been cloned from the mouse and human: i.e., PPARα, PPARγ and PPARδ. The PPARs are believed to play a role in the regulation of lipid metabolism. They can be activated by high concentration of fatty acids and have been shown to regulate the expression levels of fatty acid binding proteins or enzymes involved in fatty acid oxidation.

It has previously been discovered that a certain class of thiazolidinediones are selective PPARγ agonists (see, Willson et. al., J. Med. Chem. (1996) 39:665–668). Thiazolidinediones are a class of oral insulin-sensitizing agents that improve glucose utilization without stimulating insulin release. For instance, U.S. Pat. No. 4,287,200 discloses certain thiazolidine derivatives having the ability to lower blood glucose sugar levels. In addition, U.S. Pat. No. 4,572,912 discloses thiazolindinedione derivatives having the ability to lower blood lipid and blood sugar levels. These compounds were shown to have the ability to decrease the levels of blood lipid peroxides, blood triglycerides and blood cholesterol.

Moreover, U.S. Pat. No. 5,338,855 discloses thiazolidine derivatives containing a quinone moiety. These compounds were shown to have the ability to reduce insulin resistance in the peripheral tissues and possess the ability to suppress hepatic gluconeogenesis in the liver.

In addition to being anti-diabetic agents which can lower the concentration of glucose and lipids in the blood, U.S. Pat. No. 5,594,015 discloses thiazolidine derivatives as being effective in the treatment of hyperproliferation of epithelial cell conditions, such as psoriatic activity.

The anti-diabetic effect of the thiazolidinediones and their PPARγ agonist activity has implicated PPARγ as the molecular target for the anti-diabetic effects of thiazolidinediones. PPARγ is predominantly expressed in adipose tissue and has been implicated as a master regulator of adipocyte differentiation in pre-adipose cell lines.

In view of the role PPARγ plays in regulation of lipid metabolism and the antagonistic behavior of thiazolidinediones, there remains a need in the art for new thiazolindinedione derivatives and more effective therapies for diabetes and other ailments. The present invention fulfills these and other needs.

SUMMARY OF THE INVENTION

This invention provides new thiazolindinedione derivatives. As such, in one aspect, the present invention provides compounds of Formula I:

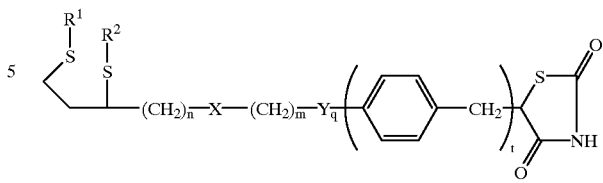

In Formula I, $R^1$ and $R^2$ are hydrogen. In an alternative embodiment, $R^1$ and $R^2$ together with the sulfurs to which they are bound join to form a 1,2-dithiolane ring. X, in Formula I, is functional group including, but not limited to O, NR, C(O)O, OC(O)O and C(O)NR, wherein R is a functional group including, but not limited to, hydrogen and optionally substituted ($C_1$–$C_6$)allyl. Y, in Formula I, is a functional group including, but not limited to, O, S and $NR^3$, wherein $R^3$ is a functional group including, but not limited to, hydrogen and optionally substituted ($C_1$–$C_6$)alkyl. In Formula I, the index "n" is an integer from 2 to 14; the index "m" is an integer from 0 to 14; the index "q" is an integer from 0 to 1; and the index "t" is an integer from 0 to 1.

In another embodiment, the present invention provides a compound of Formula II:

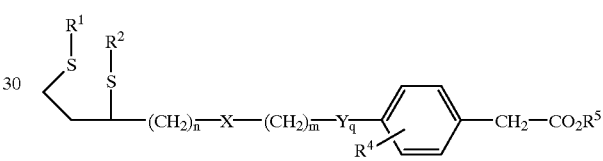

In Formula II, $R^1$ and $R^2$ are hydrogen. In an alternative embodiment, $R^1$ and $R^2$ together with the sulfurs to which they are bound join to form a 1,2-dithiolane ring. X, in Formula II, is functional group including, but not limited to O, NR, C(O)O, OC(O)O and C(O)NR, wherein R is a functional group including, but not limited to, hydrogen, optionally substituted ($C_1$–$C_6$)alkyl and optionally substituted aryl. Y, in Formula II, is a functional group including, but not limited to, O, S and $NR^3$, wherein $R^3$ is a functional group including, but not limited to, hydrogen and optionally substituted ($C_1$–$C_6$)alkyl. $R^4$, in Formula II, is a functional group including, but not limited to, hydrogen, halogen, optionally substituted ($C_1$–$C_6$)alkyl and optionally substituted ($C_1$–$C_6$)alkoxy. $R^5$, in Formula II, is a functional group including, but not limited to, hydrogen and optionally substituted ($C_1$–$C_6$)alkyl. In Formula II, the index "n" is an integer from 2 to 14; the index "m" is an integer from 0 to 14; and the index "q" is an integer from 0 to 1.

In another aspect, the present invention relates to a pharmaceutical composition comprising a compound of the Formula I wherein R, $R^1$, $R^2$ X, Y, $R^3$ n, m, q and t have the same meaning as defined above, or a pharmaceutically acceptable salt or solvate thereof, and a pharmaceutical acceptable carrier.

In another aspect, the present invention relates to a pharmaceutical composition comprising a compound of the Formula II wherein R, $R^1$, $R^2$ X, Y, $R^3$, $R^4R^5$, n, m, and q have the same meaning as defined above, or a pharmaceutically acceptable salt or solvate thereof, and a pharmaceutical acceptable carrier.

In yet another aspect, the present invention relates to a method of treating a PPARγ mediated disease, comprising administering a therapeutically effective amount of a compound of Formulae I, II or mixtures thereof, to an individual suffering from a PPARγ mediated disease. In other aspects, this invention provides methods for synthesizing the compounds of Formulae I and II.

GLOSSARY

Figure 1:
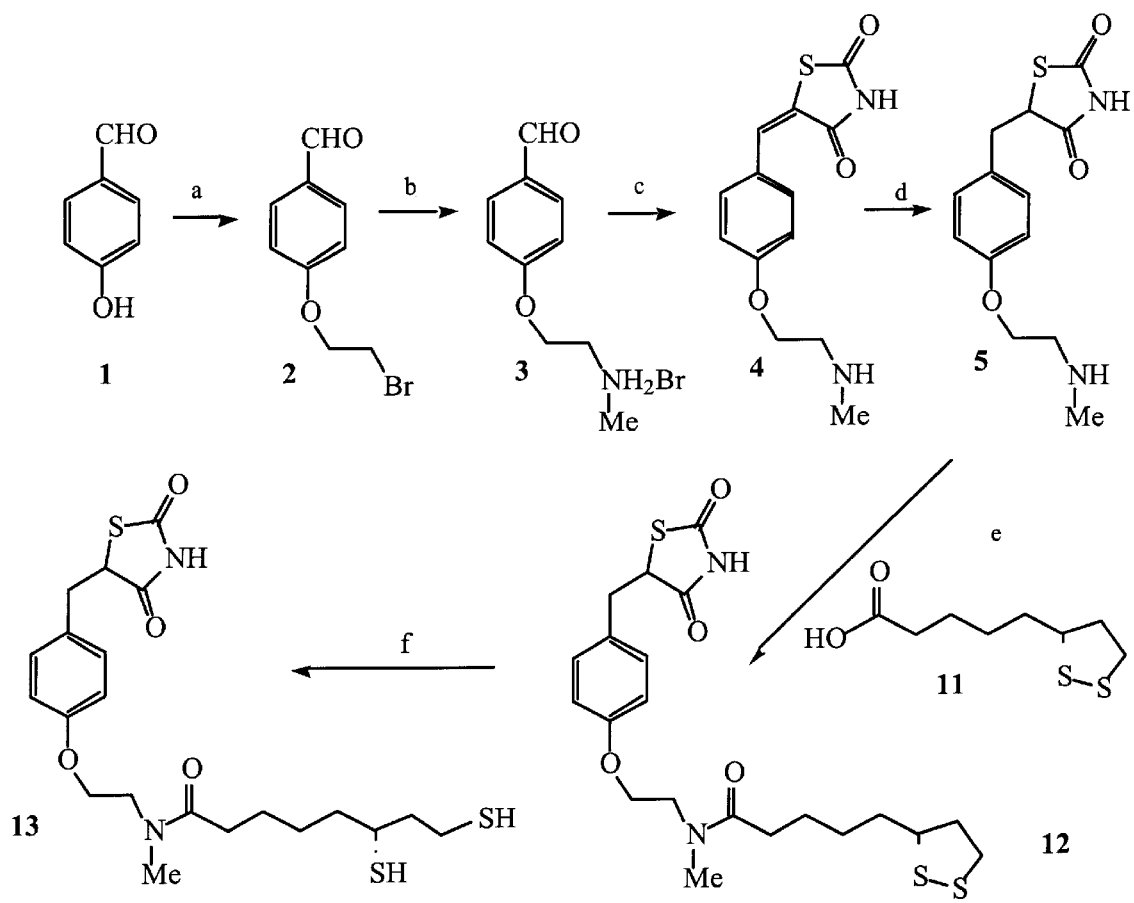
FIG. 1 illustrates a method to synthesize compounds of Group I of this invention. The following reagents are used: a) BrCH$_2$CH$_2$Br, K$_2$CO$_3$, acetone; b) MeNH$_2$, H$_2$O, MeOH; c) thiazolidine-2,4-dione, piperidine, THF; d) H$_2$, Pd/C, MeOH; e) R-(+)-α-lipoic acid), DCC, pyridine, CH$_2$Cl$_2$; f) NaBH$_4$, MeOH.

As used herein, the term "alkyl" denotes branched or unbranched hydrocarbon chains, preferably having about 1 to about 8 carbons, such as, methyl, ethyl, n-propyl, iso-propyl, n-butyl, sec-butyl, iso-butyl, tert-butyl, octa-decyl and 2-methylpentyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3--hydroxyhexyl, 2-carboxypropyl, 2-fluoroethyl, carboxymethyl, cyanobutyl and the like.

The term "alkylene" refers to a divalent alkyl group as defined above, such as methylene (—CH$_2$—), propylene (—CH$_2$CH$_2$CH$_2$—), chloroethylene (—CHClCH$_2$—), 2-thiobutene —CH$_2$CH(SH)CH$_2$CH$_2$, 1-bromo-3-hydroxyl-4-methylpentene (—CHBrCH$_2$CH(OH)CH(CH$_3$)CH$_2$—), and the like.

The term "alkenyl" denotes branched or unbranched hydrocarbon chains containing one or more carbon-carbon double bonds.

The term "alkynyl" refers to branched or unbranched hydrocarbon chains containing one or more carbon-carbon triple bonds.

The term "aryl" denotes a chain of carbon atoms which form at least one aromatic ring having preferably between about 6–14 carbon atoms, such as phenyl, naphthyl, and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

The term "acyl" denotes the —C(O)R group, wherein R is alkyl or aryl as defined above, such as formyl, acetyl propionyl, or butyryl.

The term "alkoxy" denotes —OR—, wherein R is alkyl.

The term "amido" denotes an amide linkage: —C(O)NR— (wherein R is hydrogen or alkyl).

The term "amino" denotes an amine linkage: —NR—, wherein R is hydrogen or alkyl.

The term "carboxyl" denotes —C(O)O—, and the term "carbonyl" denotes —C(O)—.

The term "carbonate" indicates —OC(O)O—.

The term "carbamate" denotes —NHC(O)O—, and the term "urea" denotes —NHC(O)NH—.

The term "EC$_{50}$" refers to the concentration of a compound required to activate 50% of the receptors that bind the compound present in a sample or a subject. Thus, in the present invention, the EC$_{50}$ of a PPARγ modifier is the concentration of the modifier that activates 50% of the PPARγ present in the sample or organism. The term "activate" has its ordinary meaning, i.e., cause to function or act.

The term "1,2-dithiolane" refers to a 5-membered heterocyclic ring consisting of two sulfur atoms at the 1 and 2 positions and carbon atoms at the remaining positions.

The term "dithiol" refers to a 1,3-dithiolpropanyl moiety.

The term "peroxisome proliferator activating receptor-gamma" or "PPARγ" refers to either the γ$_1$,γ$_2$ or γ$_3$ isotypes or a combination of all isotypes of PPARγ. PPARs are nuclear receptors which naturally bind to fatty acids and which have been implicated in adipocyte differentiation (see, Perlmann & Evans, *Cell,* 90:391–397 (1997)).

The term "unit dosage form" refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the active material and the particular effect to be achieved and (b) the limitations inherent in the art of compounding such an active material for use in humans and animals. Examples of unit dosage forms are tablets, capsules, pills, powder packets, wafers, suppositories, granules, cachets, teaspoonfuls, tablespoonfuls, dropperfuls, ampoules, vials, aerosols with metered discharges, segregated multiples of any of the foregoing, and other forms as herein described.

DETAILED DESCRIPTION OF THE INVENTION AND PREFERRED EMBODIMENTS

I. COMPOUNDS AND SYNTHESIS

This invention provides new thiazolindinedione derivatives. These compounds are useful for the treatment of certain cardiovascular diseases, certain endocrine diseases, certain inflammatory diseases, certain neoplastic (malignant) and non-malignant proliferative diseases, certain neuro-psychiatric disorders, certain viral diseases, and diseases associated with these viral infections as discussed herein. As such, in one aspect, the present invention provides a compound of Formula I:

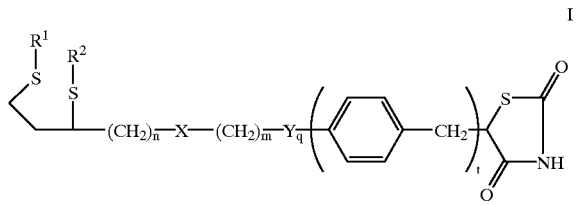

wherein R, $R^1$, $R^2$ X, Y, $R^3$ n, m, q and t have been defined above.

In the first preferred embodiment, Group I, $R^1$ and $R^2$ are hydrogen or alternatively, $R^1$ and $R^2$ together with the sulfurs to which they are bound join to form a 1,2-dithiolane ring; X is O, NR, C(O)O, OC(O)O and C(O)NR, wherein R is a functional group including, but not limited to, hydrogen, optionally substituted ($C_1$–$C_6$)alkyl, and optionally substituted aryl.

Y is O, S and $NR^3$, wherein $R^3$ is a member selected from the group consisting of hydrogen and optionally substituted ($C_1$–$C_6$)alkyl; n is an integer from 2 to 14; m is an integer from 1 to 6; q is 1; and t is 1. More preferably, n is 4, and X is COO, CONH and CON($CH_3$).

With reference to FIG. 1, the first example to be discussed in Group I, is n is 4 and m is 2, i.e., compound 12 (see, FIG. 1). This is a preferred compound because it is believed that it will furnish a naturally occurring biochemical, lipoic acid 11, upon in vivo enzymatic hydrolysis.

The synthesis of analogs 12 and 13 begins with commercially available 4-hydroxybenzaldehyde 1 and 1,2-dibromoethane. Bromoethylation to furnish O-(2-bromoethyl)benzaldehyde 2 will occur under basic conditions (see, Nate, H. et al., *Chem. Pharm. Bull.* 1987; 35(6): 2394–2411).

Figure 2:
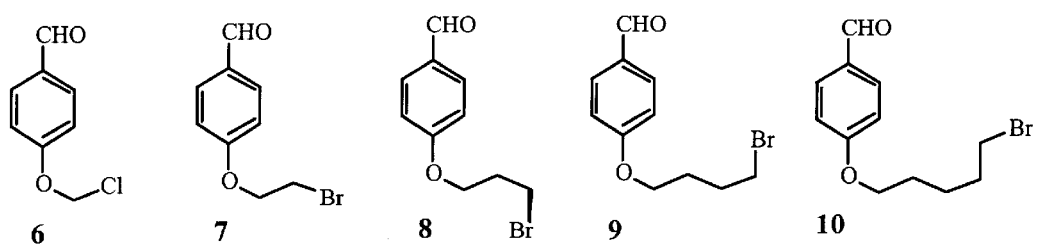
FIG. 2A–C illustrates intermediate compounds and synthesis methods of is invention. Panel A shows chemical intermediates; panel B shows chemical intermediates; and panel C shows a rutin reaction. The following reagents are used: a) ClCH$_2$CH$_2$OH, NaOH; b) H$_3$O$^+$.
Figure 2:
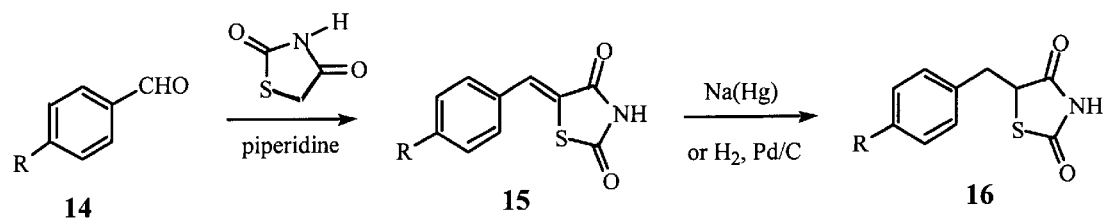
Figure 2:
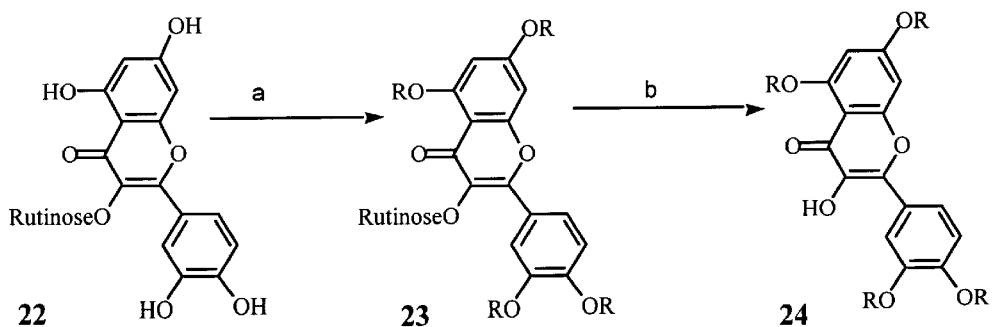

As for other chain lengths, e.g., when m is 1, 3, 4, and 5, the starting benzaldehydes 6, 8–10 have been reported in the literature (see, FIG. 2A). Aldehyde 6 has been described above along with 7. The three-carbon side chain 8, was described and prepared much in the same manner as the other bromides, i.e., alkylation of the dihaloalkane with the anion of p-hydroxybenzaldehyde (see, Schweizer, E. et al., *J. Org. Chem.* 1969; 34(1): 207–212). The four carbon aldehyde can be prepared according to the method disclosed by Ito (see, Ito S, Japanese Patent No. 01,117,867). The ortho-analog of 10 has also been prepared (see, Nate, H. et al., *Chem. Pharm. Bull.* 1987; 35(6):2394–2411).

With the bromoalkyl-benzaldehydes such as 7, $S_N2$ alkylation with excess aqueous methylamine will provide the amine 3. Storage of 3 as its amine salt prevents self condensation reactions.

Two major approaches to the 5-benzylic-1,3-thiazolidine-2,4-dione ring system have been reported, (see, FIG. 1, Yoshioka, T. et al., U.S. Pat. No. 4,572,912, Hulin, B. et al., *J. Med. Chem.* 1992; 35(10): 1853–1864, and Wilson, T. et al., *J. Med. Chem.* 1996; 39(3): 665–668).

Researchers recognized that the approach outlined in FIG. 1 was cumbersome and thus, prepared euglycemic agents containing the thiazolidinedione ring system by an exceptionally mild Aldol condensation of thiazolidinedione itself to a benzaldehyde 14 (see, FIG. 2B). The resulting arylidene thiazolidinedione 15 can then be reduced catalytically over Pd on C with hydrogen, or by the action of sodium-mercury amalgam to afford the desired ring system present in 16 (see, FIG. 2B).

With reference to FIG. 1, condensation of benzaldehyde 3 with thiazolidinedione and excess base will provide the 5-arylidene-thiazolidine-2,4-dione 4 which is easily reduced to provide the amine 5. Coupling of this secondary amine with R(+)-a-lipoic acid 11 can be achieved using standard activation of the carboxylate of 11 with species such as dicyclohexylcarbodiimide, which will lead to production of the target compound 12.

Reduction of the dithiolane group of lipoates has been reported using sodium borohydride, thus treatment of 12 with this reagent will give the potent antioxidant target dithiol 13 (see, Suzuki, Y. J. et al., *Free Radical Res. Commun.* 1993; 18:115–122).

Figure 3:
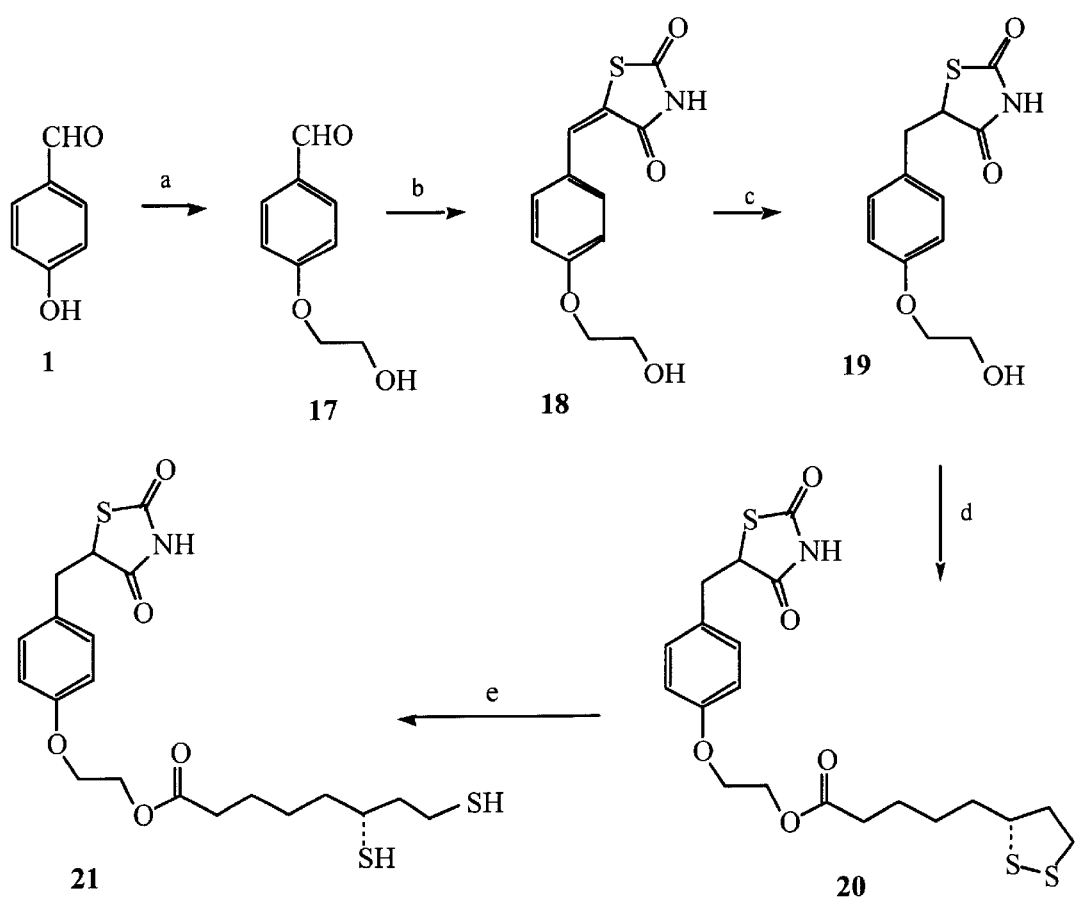
FIG. 3 illustrates a method to synthesize compounds of Group I of this invention. The following reagents are used: a) HOCH$_2$CH$_2$Cl, K$_2$CO$_3$, acetone; b) Thiazolidine-2,4-dione, piperidine, THF; c) H$_2$, Pd/C, MeOH; d) R-(+)-α-Lipoic Acid DCC, pyridine, CH$_2$Cl$_2$; e) NaBH$_4$, MeOH.

With reference to FIG. 3, the example therein is illustrative of an ester tether, i.e., X is C(O)O. Compound 20 is an example of this ester tether. Unlike the previous example of using an amino species 5 for coupling to lipoic acid 11, the corresponding alcohol is coupled. Hydroxyethylation of 1 can be accomplished under basic conditions using either ethylene oxide, or more conveniently, epichlorohydrin, as the electrophilic partner. Such reactions are common in phenol chemistry, for example, rutin has been exposed to epichlorohydrin in the presence of sodium hydroxide to give hydroxyethylated rutin 23 (see, FIG. 2C). (See, He, H. et al., *Yiyao Gongye* 1987; 18(5):205–206). Preparation of the hydroxyethoxy derivative of quercetin is completed upon hydrolysis of the sugar moiety of 23 leading to 24, wherein R=$CH_2CH_2OH$ (see, FIG. 2C).

With reference to FIG. 3, after the synthesis of 17, Aldol condensation to give the thiazolidinedione 18 will be straightforward. Reduction of 18 in a manner outlined before is not complicated and will provide the alcohol 19, ready for coupling to lipoic acid 11. Coupling of the alcohol 19 with 11 will be a slower reaction than the amine 5 with 11 (FIG. 1), and should a rate enhancement be desired, 4-N,N'-dimethylaminopyridine (DMAP) will be used as a catalyst Once the coupled target 20 is available, its reduction product 21 will be available by borohydride reduction of 20.

Figure 4:
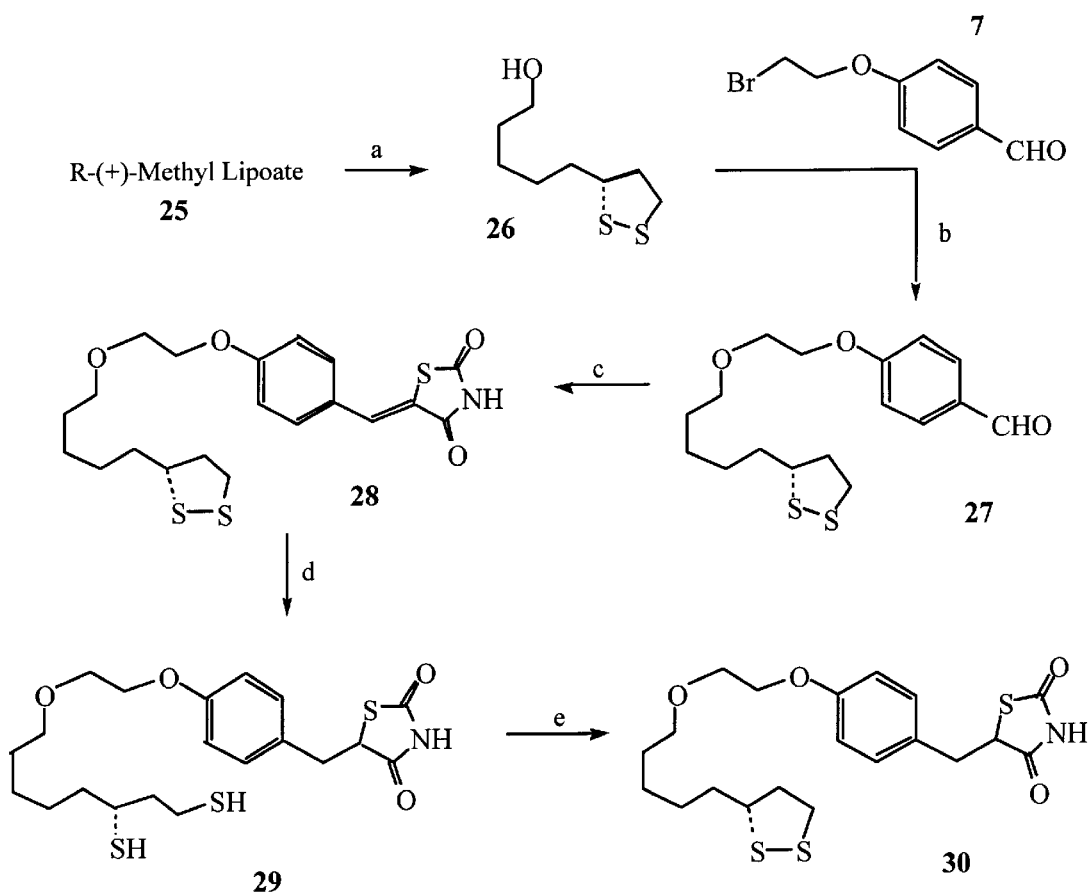
FIG. 4 illustrates a method to synthesize compounds of Group I of this invention. The following reagents are used: a) LiBH$_4$, THF; air oxidation; b) 2NaH, COCl$_2$, THF; c) thiazolidine-2,4-dione, piperidine, THF; d) H$_2$, Pd/C, MeOH; e) Air oxidation.

With reference to FIG. 4, it can be advantageous to employ an ether linkage in order to attach the lipoyl moiety to an aryl thiazolidinedione. Such an example, wherein X is oxygen, is exemplified by compound 30 wherein the natural number of carbon atoms present in lipoic acid are maintained in the molecule, and the chirality of the material is assured by starting with commercially available lipoic acid 11. In order to make this attachment, it is necessary to reduce lipoic acid to the dithiolanyl alcohol 26, and then attach this group by a Williamson ether synthesis to a benzaldehyde such as 7 as shown in FIG. 4.

The most convenient manner of reducing lipoic acid is to reduce the methyl ester 25 with a strong reducing agent such as lithium borohydride, which will also reduce the dithiolane to a dithiol. However, during workup, air oxidation will lead to oxidation to the dithiolane 26. With 26, and the synthesis of 7 outlined above, coupling of 26 and 7 will occur under anhydrous conditions with NaH to give 27. Aldol condensation to the thiazolidinedione 28 followed by reduction will provide the target dithiol 29. Exposure of the target to ambient conditions will lead to facile air oxidation to target 30.

Figure 5:
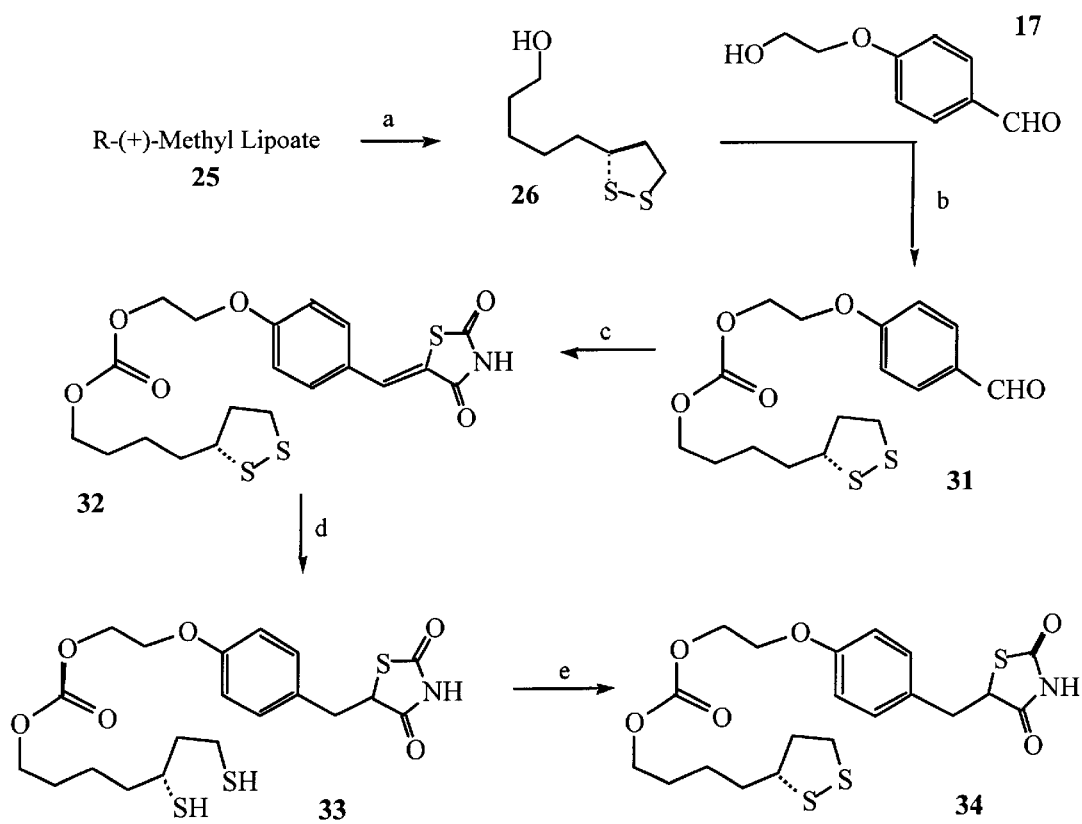
FIG. 5 illustrates a method to synthesize compounds of Group I of this invention. The following reagents are used: a) LiBH$_4$, THF; air oxidation; b) 2NaH, COCl$_2$, THF; c) thiazolidine-2,4-dione, piperidine, THF; d) H$_2$, Pd/C, MeOH; e) Air oxidation.

In another preferred embodiment of Group I, X is a carbonate i.e., OC(O)O. With reference to FIG. 5, a carbonate linkage is illustrated in compound 34, in which the antioxidant portion of the molecule is a reduced lipoate group. By starting with alcohol 26, sequential addition of alcohols 26 and 17 to phosgene will provide the mixed carbonate 31. Mild base catalyzed condensation of thiazolidinedione to the aldehyde 31 will give 32, reduction of which will give the target dithiol 33. Air oxidation of 33 then provides the target 34. Both targets can ultimately undergo in vivo metabolism of the carbonate group to furnish 26. Ensuing enzymatic oxidations will readily transform 26 into lipoic acid.

In another aspect, the present invention relates to compounds of Formula I wherein $R^1$ and $R^2$ are hydrogen, or alternatively $R^1$ and $R^2$ together with the sulfur to which they are bound join to form a 1,2-dithiolane ring; X is O, NR, C(O)O, OC(O)O and C(O)NR, wherein R is a functional group including, but not limited to, hydrogen and optionally substituted $(C_1-C_6)$alkyl. Y is O, S and $NR^3$, wherein $R^3$ is a member selected from the group consisting of hydrogen and optionally substituted $(C_1-C_6)$alkyl; n is an integer from 2 to 14; m is 0; q is 0; and t is 1. These are Group II compounds, and preferably, n is 4, and X is CONH or $CON(CH_3)$.

Figure 6:
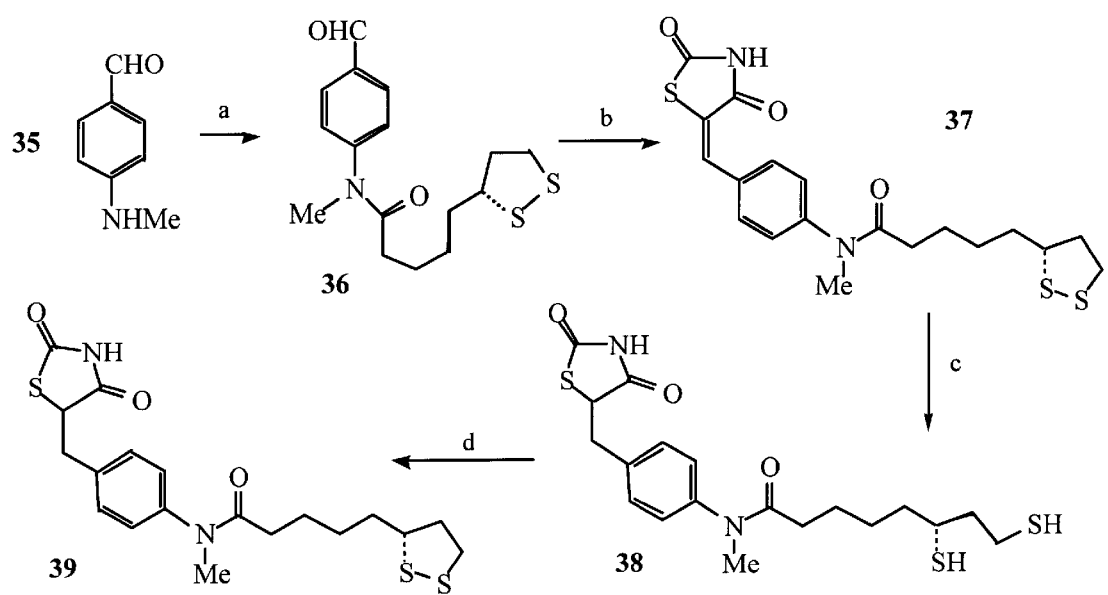
FIG. 6 illustrates a method to synthesize compounds of Group II of this invention. The following reagents are used: a) R-(+)-lipoic acid, DCC, pyridine; b) thiazolidine-2,4-dione, piperidine, THF; c) H$_2$, Pd/C, MeOH; d) air oxidation.

With reference to FIG. 6, by excluding the tether adjacent to the aromatic ring, the target compounds appear shorter. Direct attachment via an amide bond of a benzaldehyde to lipoic acid is easily accomplished, and requires only a starting amino-benzaldehyde be obtained for coupling to lipoic acid. Specifically, 35 is available by numerous synthetic routes (see, Calmes, M. et al., *Tetrahedron* 1990,46 (17), 6021–6032 and Blokhin, A. V. et al., *Khim. Geterotsikl. Soedin* 1990, 9, 1226–1229).

Coupling of 35 to lipoic acid, as described earlier will provide 36. If the active ester of lipoic acid and DCC are slow to react due to the lessened reactivity of the aniline, DMAP can be added to facilitate the reaction. After the synthesis of 36, the subsequent sequence will follow from the earlier schemes. Aldol condensation to furnish the derivative 37 can then be followed by careful reduction and aerobic workup to provide 38, which can be exposed to air to give the other desired target, 39.

Figure 7:
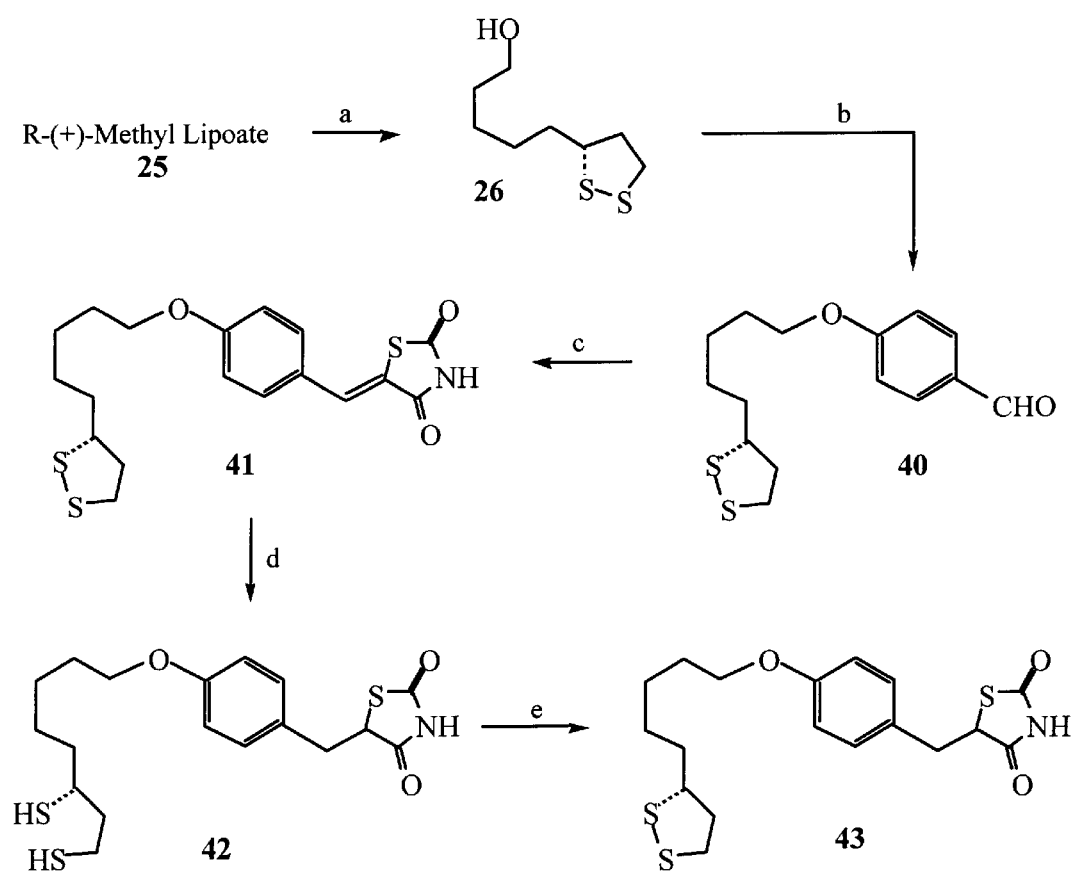
FIG. 7 illustrates a method to synthesize compounds of Group II of this invention. The following reagents are used: a) LiBH$_4$, THF; air oxidation; b) p-MePhSO$_2$Cl, NaH; then NaH, 4-hydroxybenzaldehyde; c) thiazolidine-2,4dione, piperidine, THF; d) H$_2$, Pd/C, MeOH; e) air oxidation.

In another preferred embodiment of Group II, X is oxygen. With reference to FIG. 7, direct attachment of a reduced lipoic acid, e.g., alcohol 26, to a phenol (e.g., 1) will provide a stable class of thiazolidinedione-dithiolanes and only requires a reordering of events using intermediates already described. Thus, tosylation of 26 and rapid treatment with the phenoxide anion generated from 4-hydroxybenzaldehyde 1 will give aldehyde 40. As before, once the correct benzaldehyde has been synthesized, elaboration of the tiazolidinedione moiety is straightforward. Aldol reaction of 40 to give 41; reduction to 42 and finally, and finally air oxidation to generate 43.

In yet another aspect, the present invention relates to compounds of Formula I wherein $R^1$ and $R^2$ are hydrogen, or alternatively $R^1$ and $R^2$ together with the sulfurs to which they are bound join to form a 1,2-dithiolane ring; X is O, NR, C(O)O, OC(O)O and C(O)NR, wherein R is a functional Group Including, but not limited to, hydrogen and optionally substituted $(C_1-C_6)$alkyl. Y is O, S and $NR^3$, wherein $R^3$ is a member selected from the group consisting of hydrogen and optionally substituted $(C_1-C_6)$alkyl; n is an integer from 2 to 14; m is an integer from 2 to 14; q is 0; and t is 0. These are Group III compounds and preferably, n is 4 and X is C(O)NH, and $C(O)N(CH_3)$ as in lipoamides.

Figure 8:
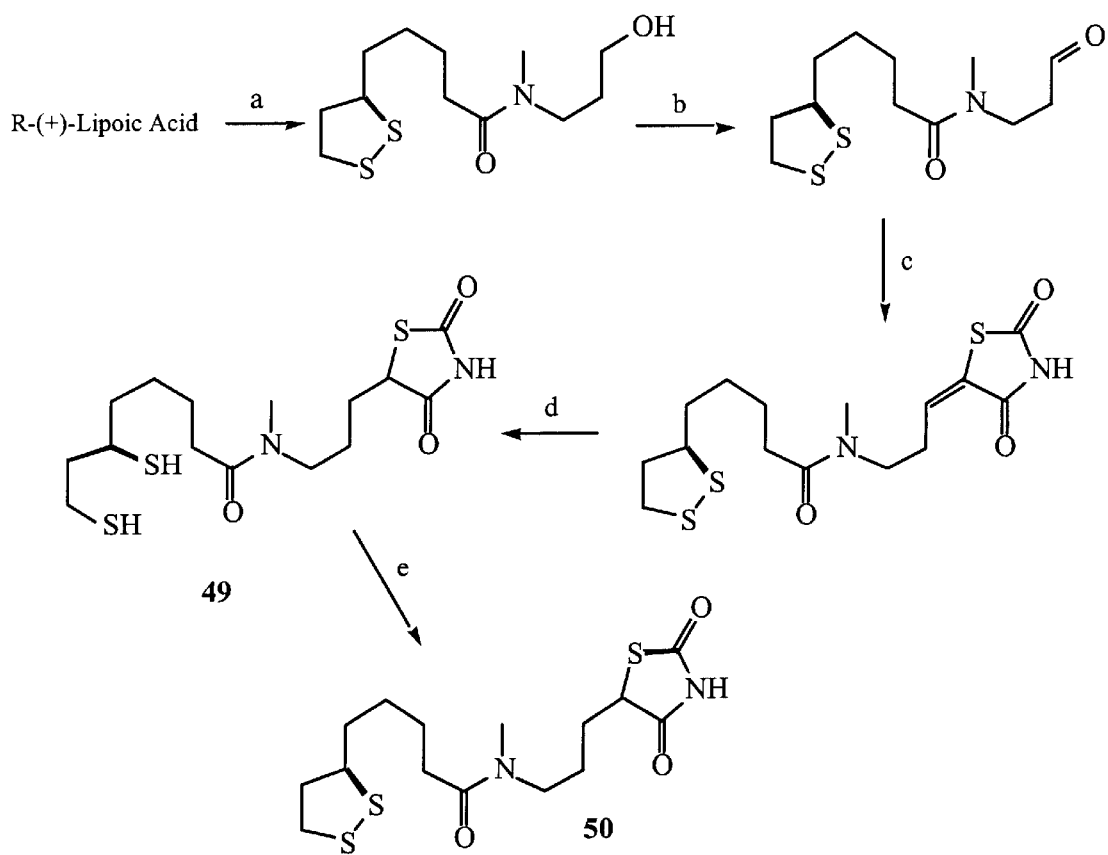
FIG. 8 illustrates a method to synthesize compounds of Group III of this invention. The following reagents are used: a) DCC, pyridine; then MeNH(CH$_2$)$_3$OH; b) NaH, 2-Fluoro-N-methylpyridinium iodide; then DMSO, Et$_3$N; c) thiazohdine-2,4dione, 2BuLi, THF; then RCHO; d) H$_2$, Pd/C, MEOH; e) air oxidation.

With reference to FIG. 8, lipoic acid coupling with commercially available N-methyl-3-amino-propanol will generate the tether wherein X is $C(O)N(CH_3)$. Subsequent reduction of the alcohol with sodium hydride will yield the aldehyde. Mild base catalyzed condensation of thiazolidinedione to the aldehyde will give the intermediate product and reduction of which will give the target dithiol (49). Air oxidation then provides the target 1,2-dithiolane (50).

Figure 9:
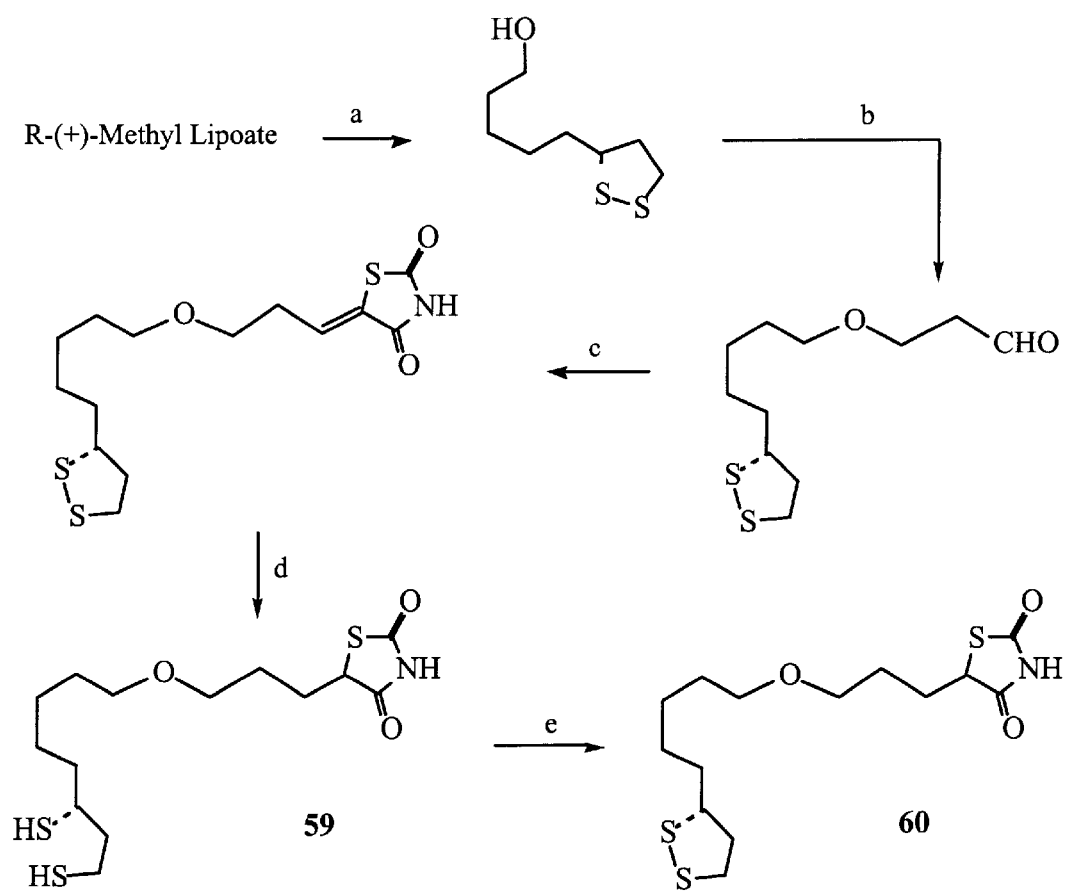
FIG. 9 illustrates a method to synthesize compounds of Group III of this invention. The following reagents are used: a) LiBH$_4$, THF; air oxidation; b) KH, ICH$_2$CH$_2$CH(OEt)$_2$; then HCl, wet THF; c) thiazolidine-2,4-dione, piperidine, THF; d) H$_2$, Pd/C, MeOH; e) air oxidation.

With reference to FIG. 9, another preferred embodiment, is when X is oxygen. The most convenient manner of reducing lipoic acid is to reduce the methyl ester with a strong reducing agent such as lithium borohydride, which will also reduce the dithiolane to a dithiol. However, during workup, air oxidation will lead to oxidation to the dithiolane. Coupling of the dithiolane and $ICH_2CH_2CH(OEt)_2$ will occur under anhydrous conditions with potassium hydride. Aldol condensation with the thiazolidinedione followed by reduction will provide the target dithiol (59). Exposure of the target to ambient conditions will lead to facile air oxidation to target 1,2-dithiolane (60).

As will be apparent to those of skill in the art, some of the compounds of Formula I exist in optical, tautomeric, stereoisomeric and isomeric forms. Although these variations have been represented herein by a single molecular formula, the present invention includes the use of individual, isolated isomers, mixtures in various proportions and racemates thereof. Preferred compounds of Formula I are set forth in Table I below.

TABLE I

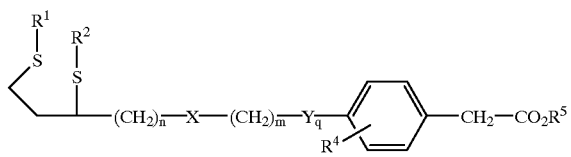

I

| COMP | R¹ | R² | n | X | m | Y | q | T |
|------|------|------|---|----------|---|---|---|---|
| 12 | 1,2 dithiolane | | 4 | C(O)NHCH₃ | 2 | O | 1 | 1 |
| 13 | H | H | 4 | C(O)NHCH₃ | 2 | O | 1 | 1 |
| 20 | 1,2 dithiolane | | 4 | C(O)O | 2 | O | 1 | 1 |
| 21 | H | H | 4 | C(O)O | 2 | O | 1 | 1 |
| 29 | H | H | 5 | O | 2 | O | 1 | 1 |
| 30 | 1,2 dithiolane | | 5 | O | 2 | O | 1 | 1 |
| 33 | H | H | 4 | OC(O)O | 2 | O | 1 | 1 |
| 34 | 1,2 dithiolane | | 4 | OC(O)O | 2 | O | 1 | 1 |
| 38 | H | H | 4 | C(O)NHCH₃ | 0 | — | 0 | 1 |
| 39 | 1,2 dithiolane | | 4 | C(O)NHCH₃ | 0 | — | 0 | 1 |
| 42 | H | H | 5 | O | 0 | — | 0 | 1 |
| 43 | 1,2 dithiolane | | 5 | O | 0 | — | 0 | 1 |
| 49 | H | H | 4 | C(O)NCH₃ | 3 | — | 0 | 0 |
| 50 | 1,2 dithiolane | | 4 | C(O)NCH₃ | 3 | — | 0 | 0 |
| 59 | H | H | 5 | O | 3 | — | 0 | 0 |
| 60 | 1,2 dithiolane | | 5 | O | 3 | — | 0 | 0 |
| 63 | H | H | 5 | O | 3 | O | 1 | 1 |
| 64 | 1,2 dithiolane | | 5 | O | 3 | O | 1 | 1 |
| 84 | 1,2 dithiolane | | 5 | N-methyl | 3 | O | 1 | 1 |
| 85 | 1,2 dithiolane | | 5 | N-pyridyl | 3 | O | 1 | 1 |

In another aspect, the present invention relates to a compound of Formula II:

II wherein R, R¹, R², R³, R⁴, R⁵, X, Y, m, n and q have been defined above.

In this aspect of the invention, compounds of Formula II can be prepared in similar fashion as outlined above for compounds of Formula I. In Formula II, structures retain the lipoate residues, but a carboxylic acid or ester replaces the thiazolidinedione ring. Compounds of Formula II have similar PPAR-γ activity and similar biological effects as do compounds of Formula I, but have altered pharmacokinetics and metabolism. The acids i.e., wherein R⁵ is a hydrogen, could be administered as ester prodrugs (i.e., wherein R⁵ is alkyl), thus enhancing their bioavailability.

Figure 10:
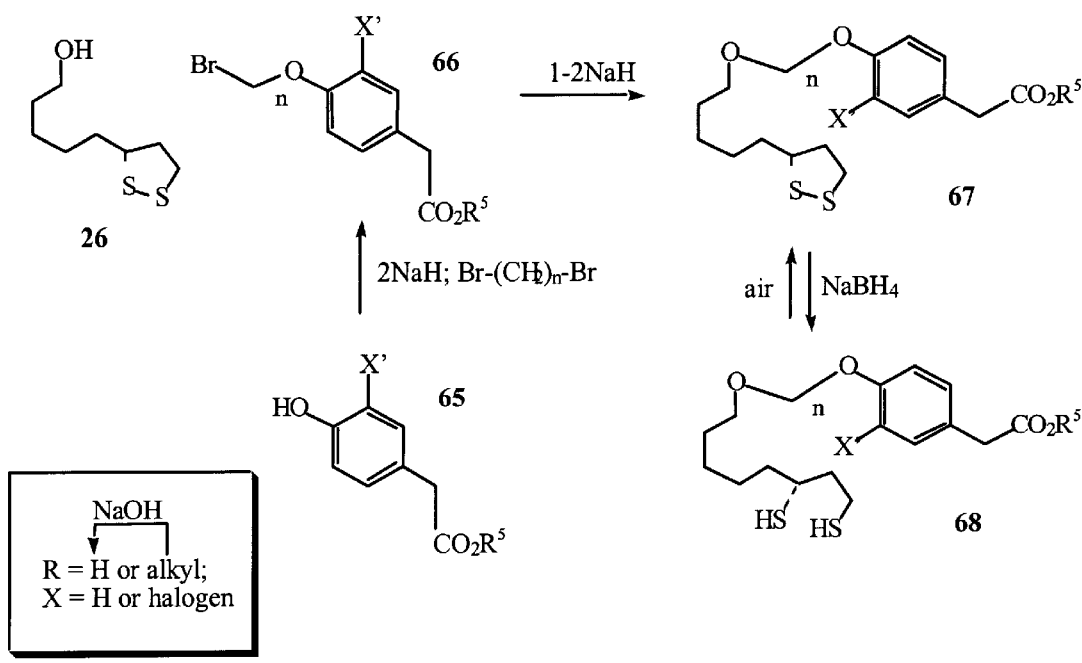
FIG. 10 illustrates a method to synthesize compounds of Formula II of the present invention.

With reference to FIG. 10, beginning with arylacetic acids and their esters such as 65 wherein X' is a halogen, alkylation of dibromoalkanes of varying carbon chain-length will lead to formation of bromoalkylethers 66. Upon formation of the anion of alcohol 26 and exposure to the bromides 66, alkylated products like 67 will be generated. The reaction will work for the dianion (wherein R⁵ is hydrogen in 65) thus requiring 2 equivalents of base to deprotonate both phenol and carboxylate. In either case, the phenoxide anion is the more reactive anion towards the dihalide, leading to 66. If 67 is produced as the ester, it can be hydrolyzed, or if 67 is produced as the acid, it can be esterified. The dithiol 68 can be produced from 67 by simple reduction in the absence of air.

Figure 11:
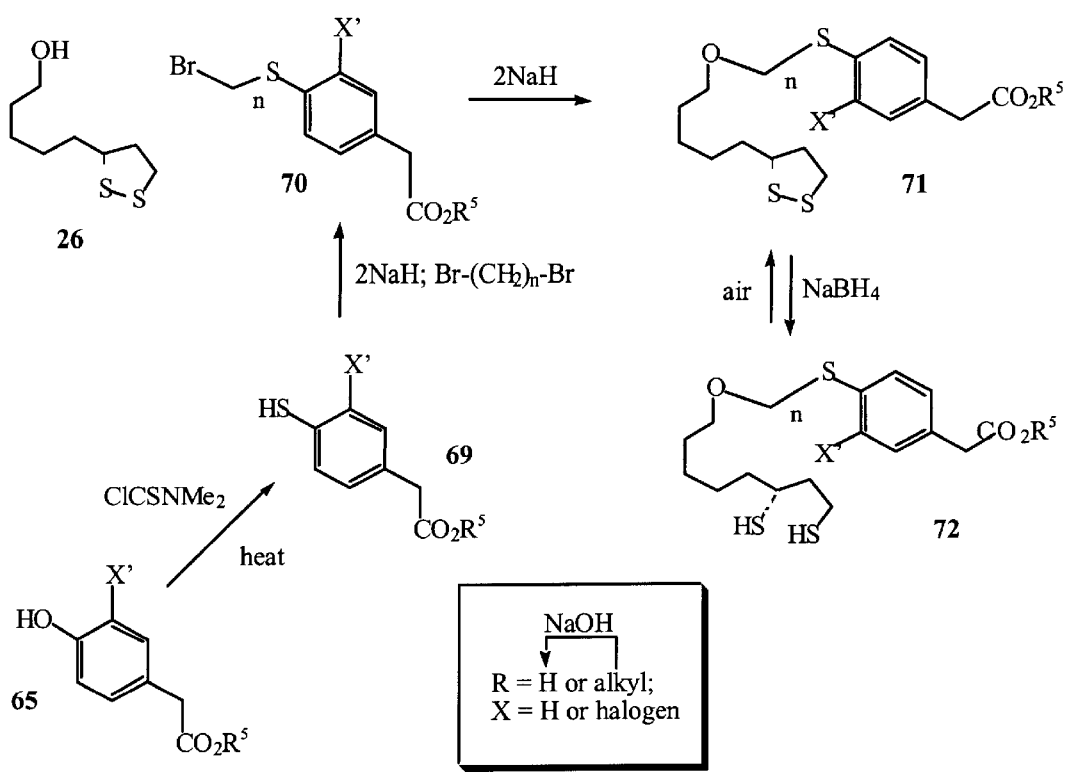
FIG. 11 illustrates a method to synthesize compounds of Formula II of the present invention.

With reference to FIG. 11, a sulfur atom can replace the phenolic linking atom. Conversion of the phenol 65 to a thiophenol 69 is possible using dimethylthiocarbonylchloride (see, Newman, et al., *Organic Synthesis*, Vol. 51, pg 139, 1971). The ensuing chemistry follows with minor modification to provide thioethers 71 or 72 wherein R⁵ is hydrogen or alkyl; and where X' is hydrogen or halogen.

Figure 12:
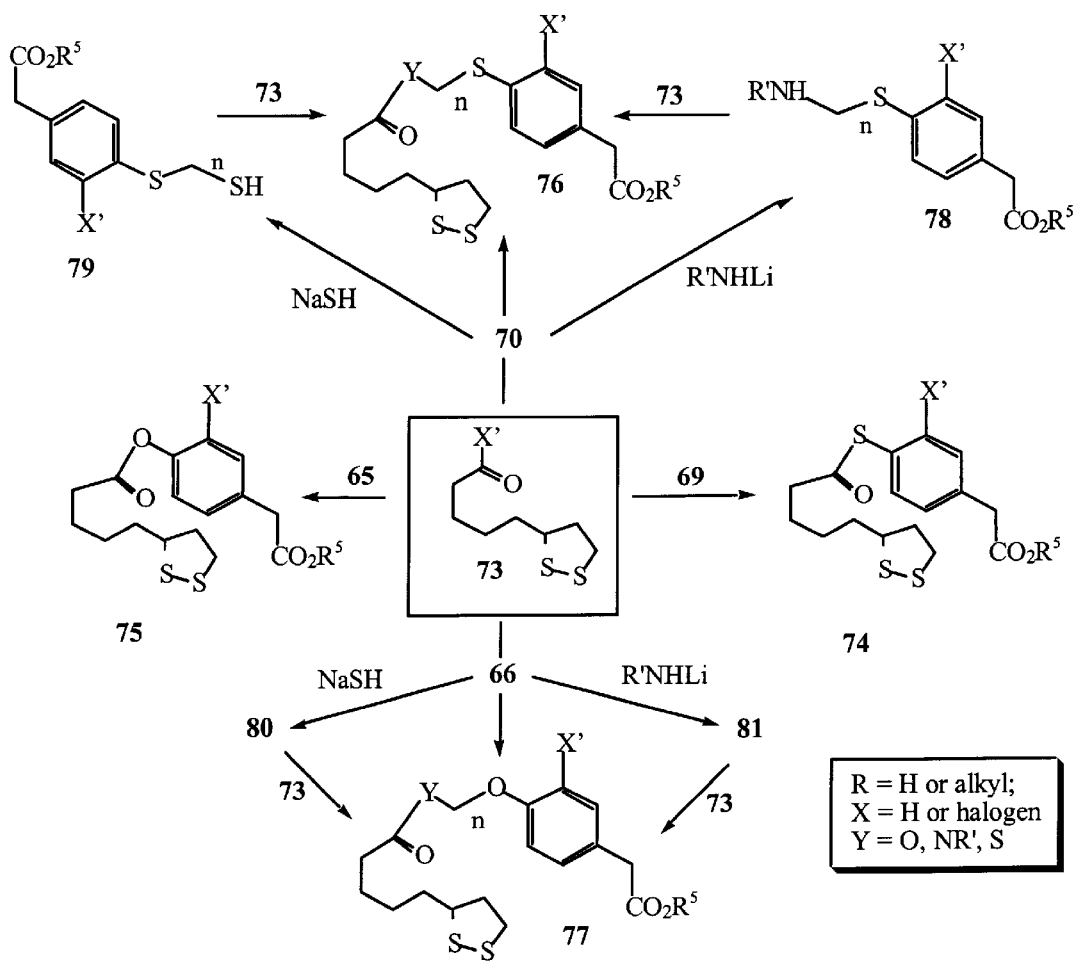
FIG. 12 illustrates a method to synthesize compounds of Formula II the present invention.

An alternative procedure of linkage of lipoic acid to either 65 or 69 to give 74 or 75 (see, FIG. 12) is possible. Either thioester 74 or ester 75 is metabolized in vivo to naturally occurring lipoic acid with regeneration of the acids/esters 65 and/or 69. The synthesis of either 74 or 75 requires simple esterification of 65 or 69 with the active ester of lipoic acid 73 (X' is Cl, OCOOEt, etc.) in the presence of a base such as pyridine or a trialkylamine. These active esters are formed directly from lipoic acid by any number of standard methods such as DCC, pyridine; oxalyl chloride, NaH; ethyl chloroformate and triethylamine, or the like.

In certain other aspects, compounds of Formula II also include other attachment methods such as esters, amides, or thioester linkages. In the case wherein X in Formula II is a ester, the previous intermediate halides 70 or 66 can be reacted with the carboxylate anion of 73 (X' is O-Metal) to give products 76 or 77 directly. In certain aspects, wherein X in Formula II is an amide, the halides are first converted to an amine or thiol by simple S_N2 chemistry. Thus, reaction of 70, for example, with LiNHR' gives the amine 78 that can then be reacted with 73 to finish 76. Alternatively, 79 can be reacted with 73 to give 76 wherein X in Formula II is a thioester.

II. CHARACTERIZATION AND PURIFICATION OF THE TARGETS

The synthetic chemistry outlined above can be carried out by standard methods apparent to those skilled in the art, and employ purification of reaction products by chromatography and/or crystallization. Product homogeneity can be ascertained by high performance liquid chromatography. A variety of columns (normal phase silica gel, reverse phase C-18, etc.) are available, as are computer workstations to analyze the results. Once reaction products are deemed greater than 99.5% HPLC pure, they can be analyzed by elemental analysis, NMR spectroscopy, FTIR, UV and EI or CI mass spectroscopy. Exact mass determinations will be possible and particularly applicable to intermediates. Other physical properties can be determined and recorded such as solubility, melting point, stability, etc. A careful study of chemical stability can be performed and suitable formulation for the oral route of administration can be examined

III. BIOLOGICAL ASSAY

Compounds of Formulae I and II are activators of PPARγ. As described hereinbelow, a transient cotransfection assay can be used to screen for PPARγ antagonist. In this assay, chimeras are constructed that fuse the ligand binding domains of three murine PPAR subtypes (α, γ and NUC-1) to the DNA binding domain of the yeast transcription factor GAL4. Expression plasmids for the GAL4-PPAR chimeras are then transfected into CV-1 cells with a reported construct containing five copies of the GAL4 DNA binding site upstream of the thymidine kinase (tk) promoter driving chloramphenicol acetyl transferase (CAT) gene expression. Using this assay system, compounds of Formulae I and II which are activators of PPARγ and not PPARα and NUC-1 are identified. (see, J. M. Lehmann et al., *J. Biol. Chem.* 270:12953–12956 (1995)).

Plasmids—GAL4-PPAR chimera expression constructs contain the translation initiation sequence and amino acids 1–76 of the glucocorticoid receptor fused to amino acids 1–147 of the yeast transcription factor GAL4, including the DNA binding domain, in the pSGS expression vector (Stratagene). cDNAs encoding amino acids 167–468, 138–440, and 174–475 of murine PPARα, NUC-1, and PPARγ1 are amplified by polymerase chain reaction and inserted C-terminal to GAL4 in the pSG5 expression vector (Stratagene) to generate plasmids pSG5-GAL4-PPARα, pSG5-GAL4-NUC-1, and pSG5-GAL4-PPARγ, respectively. The regions of the PPARs included in the chimeras should contain the ligand binding domains based on their homology to ligand binding domains of characterized nuclear receptors. The chimeras initially contained the translation start site and N-terminal 262 amino acids of the glucocorticoid receptor, including the τ1 transcriptional transactivation domain. However, as these chimeras had high basal activity in CV-1 cells, a 0.6-kilobase Bg1II fragment containing the τ1 domain can be removed, leaving the translation start site and amino acids 1–76 of the glucocorticoid receptor. Wild-type receptor expression vectors can be generated by insertion of cDNAs encoding murine PPARα, NUC-1, PPARγ1 and PPARγ2 into the expression vector pSG5 (Stratagene). Reporter plasmid (UAS)5-tk-CAT can be generated by insertion of five copies of a GAL4 DNA binding element into the BamHI site of pBLCAT2. The reporter a P2-tk-CAT was generated by insertion of the 518-bp EcoRI/XBAI fragment containing the enhancer of the aP2 gene into the BamHI site of pBLCAT2.

Cotransfection Assay—CV-1 cells are plated in 24-well plates in DME medium supplemented with 10% delipidated fetal calf serum. In general, transfection mixes contain 10 ng of receptor expression vector, 100 ng of the reporter plasmid, 200 ng of β-galactosidase expression vector (pCH110, Pharmacia) as internal control, and 200 ng of carrier plasmid. Transfections can be done with Lipofectamine (Life Technologies, Inc.) according to the manufacturers instructions. Cell extracts were prepared and assayed for chloramphenicol acetyltansferase and β-galactosidase activities as described previously.

Ligand Binding Assay—cDNA encoding amino acids 174–475 of PPARγ1 can be amplified via polymerase chain reaction and inserted into bacterial expression vector pGEX-2T (Pharmacia). GST-PPARγ LBD can be expressed in BL21(DE3)plysS cells and extracts prepared as described previously. For saturation binding analysis, bacterial extracts (100 μg of protein) is incubated at 4° C. for 3 h in buffer containing 10 mM Tris (PH 8.0), 50 mM KCl, 10 mM dithiothreitol with [$^3$H]-BRL49653 (specific activity, 40 Ci/mmol) in the presence or absence of unlabeled BRL49653. Bound can be separated from free radio-activity by elution through 1-ml Sephadex G-25 desalting columns (Boehringer Mannheim). Bound radioactivity eluted in the column void volume and can be quantitated by liquid scintillation counting.

IV. COMPOSITIONS AND METHODS

In another aspect, the present invention provides a pharmaceutical composition comprising a compound of Formula I:

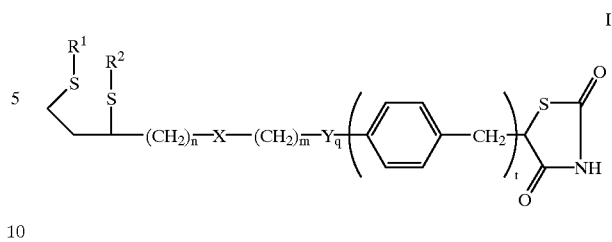

wherein R, $R^1$, $R^2$, X, Y, $R^3$ n, m, q and t have been defined above, or a pharmaceutically acceptable salt or solvate thereof, and a pharmaceutically acceptable carrier.

In yet another aspect, the present invention provides a pharmaceutical composition comprising a compound of Formula II:

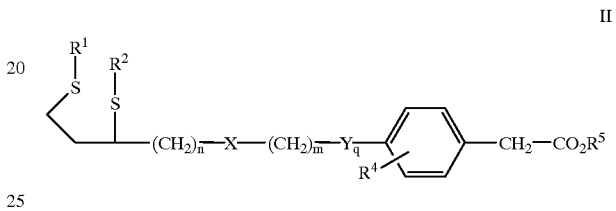

wherein R, $R^1$, $R^2$, $R^3$, $R^4$, $R^5$, X, Y, m, n and q have been defined above, or a pharmaceutically acceptable salt or solvate thereof, and a pharmaceutically acceptable carrier.

The compounds of this invention can be formulated in a variety of carriers and delivery systems. For instance, to prepare a long-acting depot formulation, a therapeutically effective concentration of the compound is placed in an oil, resin, biopolymer or other suitable delivery device as is known in the art. The amount of the therapeutic compound to be administered and the compound's concentration in depot formulations depend upon the vehicle or device selected, the clinical condition of the patient, the side effects and the stability of the compound in the formulation. Thus, the physician employs the appropriate preparation containing the appropriate concentration of the therapeutic compound and selects the amount of formulation administered, depending upon clinical experience with the patient in question or with similar patients.

In addition to the therapeutic compound, the compositions can include, depending on the formulation desired, pharmaceutically-acceptable non-toxic carriers, or diluents which include vehicles commonly used to form pharmaceutical compositions for animal or human administration. The diluent is selected so as not to unduly affect the biological activity of the combination. Examples of such diluents which are especially useful for injectable formulations are water, the various saline solutions, Ringer's solution, dextrose solution, and Hanks solution. In addition, the pharmaceutical composition or formulation may include additives such as other carriers; adjuvants; or nontoxic, non-therapeutic, non-immunogenic stabilizers and the like.

Furthermore, excipients can be included in the formulation. Examples include cosolvents, surfactants, oils, humectants, emollients, preservatives, stabilizers and antioxidants. Any pharmacologically acceptable buffer may be used, e.g., Tris or phosphate buffers. Effective amounts of diluents, additives and excipients are those amounts which are effective to obtain a pharmaceutically acceptable formulation in terms of solubility, biological activity, etc.

Thus, a composition of the invention includes a therapeutic compound which can be formulated with conventional, pharmaceutically acceptable, vehicles for topical, oral or parenteral administration. Formulations can also include small amounts of adjuvants such as buffers and preservatives to maintain isotonicity, physiological and pH stability. Means of preparation, formulation and administration are known to those of skill. See generally *Remington's Pharmaceutical Science,* 15th ed., Mack Publishing Co., Easton, Pa. (1980).

To prepare a topical formulation for the treatment of dermatological disorders listed in Tables II, III, IV & V, or diseases of the external eye (Table VII), a therapeutically effective concentration of the compound is placed in a dermatological vehicle as is known in the art. The amount of the therapeutic compound to be administered and the compound's concentration in the topical formulations depend upon the vehicle selected, the clinical condition of the patient, the side effects and the stability of the compound in the formulation. Thus, the physician employs the appropriate preparation containing the appropriate concentration of the therapeutic compound and selects the amount of formulation administered, depending upon clinical experience with the patient in question or with similar patients.

The concentration of the therapeutic compound for topical formulations is in the range of about 1 mg/mL to about 1000 mg/mL. Typically, the concentration of the therapeutic compound for topical formulations is in the range of about 2.5 mg/mL to about 25 mg/mL. Solid dispersions of the therapeutic compound as well as solubilized preparations can be used. Thus, the precise concentration is subject to modest experimental manipulation in order to optimize the therapeutic response. About 2,500 mg of therapeutic compound per 100 grams of vehicle is useful in the treatment of skin lesions to provide a 2.5% weight/weight (w/w) formulation. Suitable vehicles include oil-in-water or water-in-oil emulsions using mineral oils, petrolatum and the like as well as gels such as hydrogel.

Alternative topical formulations include shampoo preparations, oral paste, and mouth wash preparations. ORABASE7 can be used as the base oral paste to which the therapeutic compound is added. Concentrations of therapeutic compound are typically as stated above for topical formulations.

In yet another aspect, the present invention relates to a method of treating a PPARγ mediated disease, comprising administering a therapeutically effective amount of compound of the Formula I:

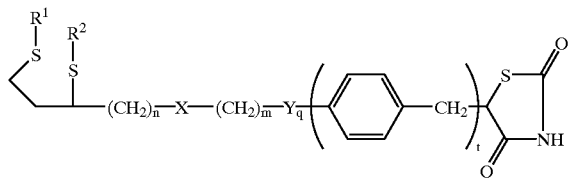

I wherein R, $R^1$, $R^2$ X, Y, $R^3$ n, m, q and t have been defined above, to an individual suffering from a PPARγ mediated disease.

In still yet another aspect, the present invention relates to a method of treating a PPARγ mediated disease, comprising administering a therapeutically effective amount of compound of the Formula II

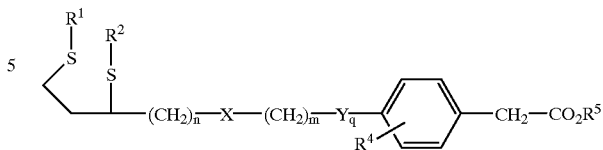

II wherein R, $R^1$, $R^2$, $R^3$, $R^4$, $R^5$, X, Y, m, n and q have been defined above, to an individual suffering from a PPARγ mediated disease.

Diseases treatable with the novel compounds described herein are outlined in Tables II, III, IV, V, VI & VII. These compounds have clinical utility in the treatment of non-malignant (Table II) and malignant (Table III) diseases in multiple organ systems, diseases caused by naked or coated DNA and RNA viruses, and local and disseminated diseases associated with the infection by these viruses (Table IV), human immunodeficiency virus (HIV) infection and diseases associated with HIV infection (Table V), neuro-psychiatric diseases (Table VI), and diseases of the eye (Table VII).

The methods of treatment provided by this invention are practiced by administering to a human or vertebrate animal in need a dose of a 1,2-dithiolane derivative compound that binds to or modifies the activity of peroxisome proliferator activated receptor-gamma (PPARγ), or a pharmaceutically acceptable salt or solvate thereof. The present method includes both medical therapeutic and/or prophylactic treatment as necessary.

The compounds described in this invention can be use to treat a variety of disorders including proliferative, inflammatory, metabolic, or infectious disorders. The specific disorders that can be treated with the compounds described in this invention are listed in Tables II, III, IV, V, VI & VII.

Using methods of the invention, therapeutic compounds are typically administered to human patients topically or orally. Parenteral administration is used in appropriate circumstances apparent to the practitioner. Preferably, the compositions are administered in unit dosage forms suitable for single administration of precise dosage amounts. For example long-acting depot compositions are administered subcutaneously or intra-muscularly as precise unit doses with each dose lasting weeks to months.

V. ADMINISTRATION

The therapeutic compound is optionally administered topically by the use of a transdermal therapeutic system (see, Barry, *Dermatological Formulations,* (1983) p. 181 and literature cited therein). While such topical delivery systems have been designed largely for transdermal administration of low molecular weight drugs, by definition they are capable of percutaneous delivery. They can be readily adapted to administration of the therapeutic compounds of the invention by appropriate selection of the rate-controlling microporous membrane.

For ophthalmic applications (Table VII), the therapeutic compound is formulated into solutions, suspensions, and ointments appropriate for use in the eye. The concentrations are usually as discussed above for topico-local preparations. For ophthalmic formulations, see Mitra (ed.), *Ophthalmic Drug Delivery Systems,* Marcel Dekker, Inc., New York, N.Y. (1993) and also Havener, W. H., Ocular Pharmacology, C. V. Mosby Co., St. Louis (1983).

The therapeutic compound is alternatively administered by aerosol. This is accomplished by preparing an aqueous aerosol, liposomal preparation or solid particles containing the compound. A nonaqueous (e.g., fluorocarbon propellent) suspension could be used. Sonic nebulizers are preferred because they minimize exposing the therapeutic compound to shear, which can result in degradation of the compound.

Ordinarily, an aqueous aerosol is made by formulating an aqueous solution or suspension of the therapeutic compound together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

For oral administration, either solid or fluid unit dosage forms can be prepared. For preparing solid compositions such as tablets, the compound of interest is mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound of interest with an inert pharmaceutical diluent and filling the mixture into a hard gelatin capsule of appropriate size. Soft gelatin capsules are prepared by machine encapsulation of a slurry of the compound of interest with an acceptable vegetable oil, light liquid petrolatum or other inert oil. Fluid unit dosage forms for oral administration such as syrups, elixirs and suspensions can be prepared. The water soluble forms can be dissolved in an aqueous vehicle together with sugar, aromatic flavoring agents and preservatives to form a syrup. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Appropriate formulations for parenteral use are apparent to the practitioner of ordinary skill. Usually, the therapeutic compound is prepared in an aqueous solution (discussed below) in a concentration of from about 1 to about 100 mg/mL. More typically, the concentration is from about 10 to 60 mg/mL or about 20 mg/mL. Concentrations below 1 mg/mL may be necessary in some cases depending on the solubility and potency of the compound selected for use. The formulation, which is sterile, is suitable for various parenteral routes including intra-dermal, intra-articular, intra-muscular, intravascular, and subcutaneous.

Slow or extended-release delivery systems, including any of a number of biopolymers (biological-based systems), systems employing liposomes, and polymeric delivery systems, can be utilized with the compositions described herein to provide a continuous or long term source of therapeutic compound. Such slow release systems are applicable to formulations for topical, ophthalmic, oral, and parenteral use.

VI. ROUTES OF ADMINISTRATION

Therapeutic agents of the invention can be delivered or administered topically or by transdermal patches for treating disorders involving the skin. Oral administration is preferred for disorders in Tables II, III, IV, V, VI & VII that cannot be treated effectively by topical therapy. Additionally, the agents can be delivered parenterally for the conditions in listed in Tables II, III, IV, V, VI & VII, that do not respond to oral or topical therapy or for conditions where oral or topical therapy is not feasible. Parenteral therapy is typically intra-dermal, intra-articular, intramuscular or intravenous.

A preferred way to practice the invention for disorders in II, III, IV, V, & VII that affect the skin is to apply the compound of interest, in a cream, lotion, ointment, or oil based carrier, directly to the skin lesions. Typically, the concentration of therapeutic compound in a cream, lotion, or oil is 1–2%. Alternatively, an aerosol can be used topically. These compounds can also be orally administered.

In general, the preferred route of administration is oral, parenteral, or topical (including administration to the eye, scalp, and mucous membranes). Topical administration is preferred in treatment of skin lesions, including lesions of the scalp, lesions of the cornea (keratitis), and lesions of mucous membranes where such direct application is practical. Shampoo formulations are sometimes advantageous for treating scalp lesions such as seborrheic dermatitis and psoriasis of the scalp. Mouthwash and oral paste formulations can be advantageous for mucous membrane lesions, such as oral lesions and leukoplakia.

Oral administration is a preferred alternative for treatment of dermatological and eye diseases listed in Tables II, III, IV, V, VI & VII where direct topical application is not useful, and it is a preferred route for other non-dermatological applications. Intravenous administration may be necessary in disorders that cannot be effectively treated by topical or oral administration. Intra-articular injection is a preferred alternative in cases of arthritis (psoriatic or nonpsoriatic) where the practitioner wishes to treat one or only a few (such as 2–6) joints. Usually, the compound is delivered in an aqueous solution of about 10–20 mg/mL. Additionally, the therapeutic compounds are injected directly into lesions (intra-lesion administration) in appropriate cases. Intradermal administration is an alternative for dermal lesions.

For pulmonary applications, a chemical delivery system for drug targeting to lung tissue using a compound of Formulae I or II or mixtures thereof as the “targetor moiety”. Therefore a preferred therapeutic compound is compound 3 that modifies the activity of PPARγ and is formulated into solutions, suspensions, aerosols and particulate dispersions appropriate for application to the pulmonary system. The therapeutic agent may be inhaled via nebulizer, inhalation capsules, inhalation aerosol, nasal solution, intratracheal as a solution via syringe, or endotracheal tube as an aerosol or via as a nebulizer solution. In vitro kinetic and in vivo pharmacokinetics studies have shown that the compounds of Formulae I or II or mixtures thereof, provide an effective pulmonary delivery system which, in a sufficiently stable in buffer and biological media, is hydrolyzed rapidly into the respective active parent drugs, with significantly enhanced delivery and retention of the active compound to lung tissue.

VII. DOSAGE AND SCHEDULES

An effective quantity of the compound of interest is employed in treatment. The dosage of compounds used in accordance with the invention varies depending on the compound and the condition being treated. The age, weight, and clinical condition of the recipient patient; and the experience and judgment of the clinician or practitioner administering the therapy are among the factors affecting the selected dosage. Other factors include the route of administration the patient, the patient’s medical history, the severity of the disease process, and the potency of the particular compound. The dose should be sufficient to ameliorate symptoms or signs of the disease treated without producing unacceptable toxicity to the patient.

Broadly, an oral dosing schedule is from about 100 to about 600 mg twice a day. More typically, a single dose is about 100–200 mg of compound given twice a day. A convenient oral dose for an adult patient is 200 mg twice a day. A dosage range for topical treatment is about 0.1% to about 10% (weight/volume) in a cream or ointment, applied twice a day. A usual dose for intra-articular injection is 20–40 mg injected per joint, not generally exceeding three joints per therapy session. A typical dosage for intra-dermal administration is about 20–75 mg per injection per site. A typical dosage for intravenous or intramuscular administration in an adult patient would be between 1 mg and 1000 mg per day given in single or divided doses depending on the judgment of the practitioner.

In some aspects the oral dose is determined from the following formula:

$$\text{Oral dose (in milligrams)} = (k_1)(EC_{50})(k_2)(LBW)(MW);$$

wherein k, is a dimensionless constant with values ranging from 5 to 100; $EC_{50}$ is in mol/L; $k_2$ is the fractional water content of the lean body weight (LBW) of the patient=0.72 L/kg, (see, *GEIGY SCIENTIFIC TABLES*, VOL 1 , Lentner (ed.), p217, Ciba-Geigy Limited, Basle, Switzerland (1981); and MW is the molecular weight of the drug in g/mol.

Typically, the dosage is administered at least once a day until a therapeutic result is achieved. Preferably, the dosage is administered twice a day, but more or less frequent dosing can be recommended by the clinician. Once a therapeutic result is achieved, the drug can be tapered or discontinued. Occasionally, side effects warrant discontinuation of therapy. In general, an effective amount of the compound is that which provides either subjective relief of symptoms or an objectively identifiable improvement as noted by the clinician or other qualified observer.

The compounds in this invention can also be given orally in combination with compounds that bind or modify the activity of the vitamin D receptor or in combination with compounds that bind or modify the activity of the retinoid X receptors or retinoic acid receptors to provide for a synergistic effect in the treatment or prevention of the disorders listed in Tables II, III, IV, V, VI & VII. Examples of such compounds that provide for synergistic effect when given in combination with the drugs encompassed by the current invention include vitamin D analogs, various retinoic acid derivatives, and other ligands for retinoid X receptors or retinoic acid receptors including but not limited to compounds such as LG100268, tazarotene, TTNPB, or LGD1069 (Targretin).

Synergistic therapeutic effects can be achieved by oral administration of the drugs encompassed in the current invention together with orally or intravenously administered drugs that bind to and or modify the activity of either the vitamin D receptor or retinoid X receptors or retinoic acid receptors. As such, in another embodiment, the present invention relates to a method of treating a PPARγ mediated disease, comprising administering a combination therapy of a compound of Formulae I or II and a member selected from the group consisting of a drug that bind to or modifies the activity of a vitamin D receptor, a retinoid X receptor, or a retinoic acid receptor.

A preferred dosage range for administration of a retinoic acid derivative or retinoid would typically be from 0.1 to 100 mg per square-meter of body surface area, depending on the drug's ability to bind to or modify the activity of its cognate nuclear receptor, given in single or divided doses, orally or by continuous infusion, two or three times per day. For synergistic therapy, the preferred dosages and routes and frequency of administration of the vitamin D analogs or retinoid compounds can be similar to the dosages and routes and frequency of administration ordinarily recommended for these agents when given without compounds of Formulae I or II. Examples of effective retinoids are 9-cis-retinoic acid, 13-cis-retinoic acid, all-trans-retinoic acid (at-RA). Preferred retinoids for this purpose would include 13-cis-retinoic acid, tazarotene, or Targretin. A preferred dosage range for systemic administration of a vitamin D analog would typically be from 0.1 to 100 mg per square-meter of body surface area, depending on the drug's ability to bind to and or activate its cognate vitamin D receptor, given in single or divided doses, orally or by continuous infusion, two or three times per day. Examples of effective vitamin D analogs are 1,25-dihydroxy-vitamin D (1,25-(OH)2-vit D) and calcipotriene. The dosage range and routes and frequency of administration of compounds of Formulae I or II required to achieve synergistic effects when given with vitamin D or retinoid derivatives are the same as those described elsewhere in this disclosure. The preferred mode of administration of these drugs for synergistic therapeutic purposes would be orally although alternatively one can use topical or parenteral routes of administration. Synergistic therapeutic effects can also be achieved for conditions that are treated by topical administration of vitamin D derivatives or retinoid related compounds such as psoriasis, acne, or other disorders not involving the skin described in Tables II, III, IV, V, VI & VII. The dosages and the modes and frequency of administration of the vitamin D or retinoid related compounds for synergistic topical therapy would be similar to those ordinarily recommended for these agents when given without compounds of Formulae I or II. The dosage range and the modes and frequency required for topical administration of the compounds of Formulae I or II given in combination with vitamin D or retinoid related compounds are the same as those described elsewhere in this disclosure.

The foregoing is offered primarily for purposes of illustration. It will be readily apparent to those of ordinary skill in the art that the operating conditions, materials, procedural steps and other parameters of the system described herein may be further modified or substituted in various ways without departing from the spirit and scope of the invention. For example, the invention has been described with human patients as the usual recipient, but veterinary use is also contemplated.

VII. EXAMPLES

General

All reactions were carried out under an argon atmosphere with dry, freshly distilled solvents under anhydrous conditions, unless otherwise stated. Acetone was distilled from potassium carbonate, and N, N-dimethylformamide (DMF), from calcium hydride. Yields were applied to chromatographically and spectroscopically ($^1$H-NMR) homogeneous materials. Reagents were purchased at highest commercial quality and used without further purification unless otherwise mentioned. Reactions were monitored by thin-layer chromatography carried out on 250 microns Analtech, Inc. silica gel plates, employing UV light and p-anisaldehyde solution and heat to visualize the distributions of compounds. Silica gel (60 Å, 230–400 mesh) (Whatman Inc.) was used for flash column chromatography.

Preparative thin-layer chromatography (PTLC) separations were carried out on 1000 microns silica gel plates (Analtech). NMR spectra were obtained by Bruker Advance DXR-400 or DXR-300 instruments and calibrated using tetramethylsilane. Abbreviations were used to explain multiplicities as followings: s=singlet, d=doublet, t=triplet, q=quartet, qui=quintet, m=multiplet, b=broad.

Example 1

This example illustrates the synthesis of compounds 63 and 64

A. The synthesis of compound 8.

Figure 13:
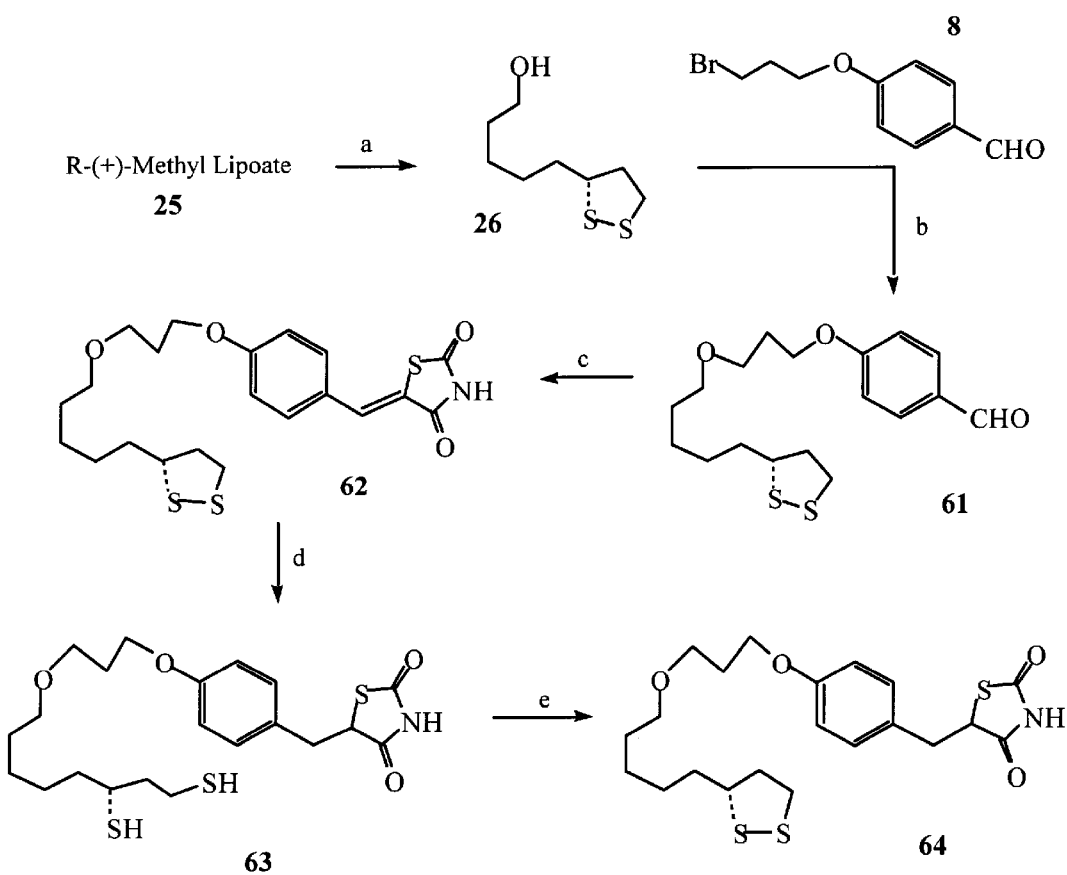
FIG. 13 illustrates a method to synthesize compounds of the present invention. The following reagents were used: a) LiBH$_4$, THF; air oxidation; b) NaH, THF or DMF; c) thiazolidine-2,4-dione, piperidine, THF, or piperidine, benzoic acid; d) H$_2$, Pd/C, MeOH; e) air oxidation.

With reference to FIG. 13, $K_2CO_3$ (1.82 g, 13 mmol) and 1,3-dibromopropane (3.05 mL, 30 mmol) were added to a solution of 4hydroxy-benzaldehyde (1.22 g, 10 mmol) in acetone (30 mL). The mixture was heated under reflux for 8.5 hrs. Then the reaction mixture was filtered and the solvent was removed by evaporation. The resulting residue was mixed with ether and then washed consecutively with 5% NaOH, water, and brine. After drying with $MgSO_4$ and evaporation of the solvent, flash column chromatography (silica gel, hexane 100%>EtOAc: hexane=10:90>20:80) gave the desired compound as a pale yellow oil: Rf=0.71 (silica gel, EtOAc: hexane=35:65); yield 61%; $^1$H-NMR (300 MHZ, $CDCl_3$) δ9.86 (1H, s), 7.82–7.79 (2H, dd, J=6.9 and 1.8 Hz), 7.00–6.97 (2H, dd, J=7.1 and 1.6 Hz), 4.19–4.15 (2H, t, J=5.8 Hz), 3.61–3.56 (2H, t, 6.4 Hz), 2.37–2.28 (2H, qui, 6 Hz).

B. The synthesis of compound 61.

With reference to FIG. 13, to a methyl lipoate (25) solution in dry THF (10 grams or 45 mmol, in 500 mL) at 0° C. under argon was added a 1M $LiBH_4$ solution in THF (50 mmol or 50 mL). After the reduction was complete by TLC, the mixture was acidified with dilute HCl in water, and extracted 3×150 mL diethyl ether. The combined organic layer was dried over $NaSO_4$, and the solvent was removed by rotary evaporation to provide 26 as a thick oil. Upon treatment of a suspension of NaH (1.4 grams of a 48% oil dispersion, washed free of oil with hexane, 30 mmol) in dry THF (50 mL) under argon with 26 in dry THF (5 grams or 26 mmol in 100 mL) hydrogen gas is evolved with formation of the sodium salt of 26. Addition of a THF solution of the bromobenzaldehyde 8 prepared in part A above, (30 mmol in 50 mL) leads to formation of sodium bromide and the desired product. Water is added (1 L) and the mixture is extracted 3×100 mL ethylacetate. The combined organic layer was dried over $NaSO_4$, filtered, and the solvent evaporated to give the aldehyde 61. The aldehyde is then purified by crystallization or column chromatography.

C. Synthesis of the Aldol adduct compound 62.

A solution of the benzaldehyde 61 (5 grams or 14 mmol) in ethanol (100 mL) was treated with piperidine (0.5 mL) and heated at reflux. Alternatively, the benzaldehyde could be treated in benzene with piperidinium benzoate (0.5 grams) with azeotropic removal of water. In either case, when the reaction was judged complete by TLC, the reaction mixture is poured into water and extracted with EtOAc (3×100 mL); the combined organic layer is then dried over $NaSO_4$, filtered, and the solvent removed to give the Aldol adduct 62.

D. Synthesis of the 1,2 dithiolane compound 64.

The purified Aldol adduct 62 (2 grams or 4.4 mmol) in ethanol (50 mL) is treated with excess 10% Pd/C (5 g), or with a similar quantity of S-resistant Pd/C, and placed under an atmosphere of hydrogen with stirring. When reduction was complete by TLC, the Pd/C was removed by filtration under argon, and the solvent was evaporated with care to avoid exposure to air, leading to the dithiol 63. Exposure of 63 to air will generate the dithiolane 64 that could be purified by crystallization or chromatography.

Example 2

This example illustrates a clinical trial and therapy by topical application.

A patient having dermal manifestations of either psoriasis vulgaris, or acne vulgaris, or human papilloma virus (HPV) infection (e.g., anogenital warts) is selected for therapy using the invention. A compound of Formulae I or II that modifies the activity of PPARγ is prepared in a cream vehicle at a concentration of 1 to 5% (weight/volume), typically 2.5% and is applied to the affected skin three times a day. After the skin lesions have subsided, therapy is discontinued.

Example 3

This example illustrates a clinical trial and therapy by oral administration.

A patient having type 2 diabetes mellitus, or chronic generalized acne, or chronic generalized psoriasis, with or without psoriatic arthritis, or rheumatoid arthritis, or inflammatory bowel disease (e.g., ulcerative colitis) is selected for therapy. The patient weighs 80 kilograms. For infants or children the doses suggested are lowered in a linear fashion based on body weight or surface area. The female patient of child-bearing potential is given a pregnancy test to confirm that the patient is not pregnant. Provided that the patient is not pregnant and does not plan to become pregnant during treatment, a compound of Formulae I or II that modifies the activity of PPARγ is orally administered in a dosage of 20 to 1,000 milligrams twice daily, more typically 100 mg twice daily. The patient is monitored for improvement in the manifestations of the index disease. Additionally, a complete blood count, including white cell count and differential, a platelet count, and liver function tests (such as levels of alkaline phosphatase, lactose dehydrogenase, and transaminases) are checked prior to treatment and periodically thereafter. The dosage is tapered when the manifestations of the disease subside, or discontinued if indicated.

Example 4

This example illustrates a clinical trial and therapy by intravenous injection administration.

A patient having non-metastatic cancer, such as breast cancer, prostate cancer or colon cancer is selected for therapy. The patient weighs 80 kilograms. For infants or children the doses suggested are lowered in a linear fashion based on body weight or surface area. The female patient of child-bearing potential is given a pregnancy test to confirm that the patient is not pregnant. If indicated, the tumor is surgically excised. When the patient is stable post-surgically, a compound of Formulae I or II that modifies the activity of PPARγ administered intravenously in a dose of 50 to 1,000 mg, more typically in a dosage of 200 milligrams, as a bolus or continuous infusion over 4 hr, every 12 hr. The patient is monitored for improvement in his or her manifestations of the cancer in terms of laboratory tests such as prostate specific antigen (PSA) for prostatic cancer, or carcinoembryonic antigen (CEA) for breast or colon cancer. Additionally, a complete blood count, including white cell count and differential, a platelet count, and liver function

Example 5

This example illustrates a clinical trial and therapy by intralesional injection administration.

The patient is one who has venereal warts (HPV infection), or dermatological manifestations of Kaposi sarcoma (with or without infection with the human immunodeficiency virus) who is not a candidate for surgery, or in whom surgery may impair bodily functions (such as painful sexual activity, or impairment in urination or defecation in the case of venereal warts). The patient is treated by administering, intralesionally, injection(s) of a compound of Formulae I or II that modifies the activity of PPARγ. The compound is administered in a 5 to 50 mg/mL, more typically 20 mg/mL of an aqueous solution, a suspension or an emulsion. About 10–75 mg are injected directly into each lesion, depending on its size and volume. The therapy is repeated weekly until the lesions are eradicated.

Example 6

This example illustrates a clinical trial and therapy by intra-articular injection administration.

A patient having psoriatic arthritis or rheumatoid arthritis with painful, swollen, inflamed joints, is treated with intra-articular injection(s) of a compound of Formulae I or II that modifies the activity of PPARγ. The compound is administered in a 5 to 50 mg/mL, more typically 20 mg/mL of an aqueous solution, a suspension or an emulsion. About 10–50 mg are injected directly into each joint, depending on the joint and the severity of the disease. The therapy is repeated weekly until the disease subsides and the pain and inflammation resolves.

Example 7

This example illustrates a clinical trial and therapy by intrathecal injection administration.

A patient having viral meningitis (e.g., meningitis caused by cytomegalovirus), is treated with intrathecal injection(s) of a compound of Formulae I or II that modifies the activity of PPARγ. The compound is administered by injection or via catheter, in a 5 to 50 mg/mL (more typically 20 mg/mL) of an aqueous solution, a suspension or an emulsion. About 10–50 mg, depending on the patient's lean body-mass and the severity of the disease, is injected directly into the intrathecal space. The therapy is administered 3 time a week and tapered to once weekly as symptoms subside, and eventually discontinued when the infectious agent is eradicated.

Example 8

This example illustrates a clinical trial for prophylaxis or therapy of ocular disease by topical application.

For ophthalmic applications, the therapeutic compound is a compound of Formulae I or II that modifies the activity of PPARγ and is formulated into solutions, suspensions, and ointments appropriate for application to the external eye. The formulation contains the drug at a concentration of 20 mg/mL. A patient having allergic conjunctivitis, or viral conjunctivitis, or keratitis, corneal ulceration or uveitis (secondary to surgical procedures or contact lens injury) is treated by topico-local administration of the optic formulation, with 2 to 3 drops being instilled in each eye and the process repeated every 4 hr for 2 wk or more, depending on the type or severity of the disease, until the symptoms have subsided or resolved.

Example 9

This example illustrates a clinical trial for pulmonary therapy.

A compound of Formulae I or II is used and is formulated into solutions, suspensions, aerosols and particulate dispersions appropriate for application to the pulmonary system. The patient weighs 80 kilogram. For infants or children the doses suggested are lowered in a linear fashion based on body weight or surface area. The patient has asthma or COPD. The therapeutic agent may be inhaled via nebulizer, inhalation capsules, inhalation aerosol, nasal solution, intratracheal as a solution via syringe, or endotracheal tube as an aerosol or via as a nebulizer solution. For delivery via nebulizer, the therapeutic agent is given at a dose of 0.5 to 50 mg per 2 mL solution, more typically 10 mg/2 mL dose given every 15 min as needed for acute treatment. For delivery by metered dose inhaler, the therapeutic agent is given at a dose of 0.05 to 1.0 mg per actuation, more typically 0.2 mg per actuation, given every 4 hr.

TABLE II

Examples of non-malignant proliferative, inflammatory disorders treatable with compounds described in this invention

| Organ System | Disease/Pathology |
| --- | --- |
| Dermatological | Psoriasis (all forms), acne vulgaris, acne rosacea, common warts, anogenital (venereal) warts, eczema; lupus associated skin lesions; dermatitides such as seborrheic dermatitis and solar dermatitis; keratoses such as seborrheic keratosis, senile keratosis, actinic keratosis, photo-induced keratosis, skin ageing, including photo-induced skin aging, keratosis follicularis; keloids and prophylaxis against keloid formation; leukoplakia, lichen planus, keratitis, contact dermatitis, eczema, urticaria, pruritus, hidradenitis, acne inversa. |
| Cardiovascular | Hypertension, vasculo-occlusive diseases including atherosclerosis, thrombosis and restenosis after angioplasty; acute coronary syndromes such as unstable angina, myocardial infarction, ischemic and non-ischemic cardiomyopathies, post-MI cardiomyopathy and myocardial fibrosis, substance-induced cardiomyopathy. |

TABLE II-continued

Examples of non-malignant proliferative, inflammatory disorders treatable with compounds described in this invention

| Organ System | Disease/Pathology |
|---|---|
| Endocrine | Insulin resistant states including obesity, diabetes mellitus (types 1 & 2), diabetic retinopathy, macular degeneration associated with diabetes, gestational diabetes, impaired glucose tolerance, polycystic ovarian syndrome; osteoporosis, osteopenia, accelerated aging of tissues and organs including Werner's syndrome. |
| Urogenital | Endometriosis, benign prostatic hyperplasia, leiomyoma, polycystic kidney disease, diabetic nephropathy. |
| Pulmonary | Asthma, chronic obstructive pulmonary disease (COPD), reactive airway disease, pulmonary fibrosis, pulmonary hypertension. |
| Immunological/ Connective tissue/ Joints | Rheumatoid arthritis, Raynaud's phenomenon/disease, Sjogren's syndrome systemic sclerosis, systemic lupus erythematosus, vasculitides, ankylosing spondylitis, osteoarthritis, reactive arthritis, psoriatic arthritis, fibromyalgia. |
| Other | Fibrocystic breast disease, fibroadenoma, chronic fatigue syndrome. |

TABLE III

Examples of neoplastic diseases or malignancies diseases treatable with compounds described in this invention

| Organ System | Malignancy/Cancer type |
|---|---|
| Skin | Basal cell carcinoma, melanoma, squamous cell carcinoma; cutaneous T cell lymphoma; Kaposi's sarcoma. |
| Hematological | Acute leukemia, chronic leukemia and myelodysplastic syndromes. |
| Urogenital | Prostatic, renal and bladder carcinomas, anogenital carcinomas including cervical, ovarian, uterine, vulvar, vaginal, and those associated with human papilloma virus infection. |
| Neurological | Gliomas including glioblastomas, astrocytoma, ependymoma, medulloblastoma, oligodendroma; meningioma, pituitary adenoma, neuroblastoma, craniopharyngioma. |
| Gastrointestinal | Colon, colorectal, gastric, esophageal, mucocutaneous carcinomas. |
| Breast | Breast cancer including estrogen receptor and progesterone receptor positive or negative subtypes, soft tissue tumors. |
| Metastasis | Metastases resulting from the neoplasms. |
| Other | Angiomata, angiogenesis associated with the neoplasms. |

TABLE IV

Examples of viral infections and related pathologies treatable with compounds described in this invention

| Virus | Viral infection/cancer or other virus-associated pathology |
|---|---|
| HTLV | T-cell leukemia/lymphoma, HTLV-associated arthritides/myelopathies. |
| HPV | Cervical and anogenital cancers; common and anogenital (venereal) warts, including verrucae, condyloma or condyloma acuminata, related non-neoplastic (e.g., keratitis, conjunctivitis) pre-neoplastic and neoplastic (e.g., conjunctival epithelial neoplasms) diseases of the eye. |
| HAV, HBV, HCV | Hepatitis, hepatocellular carcinoma, lymphoma. |
| CMV | Hepatitis, retinitis, meningitis. |
| HSV, VSV | Related mucocutaneous, oropharyngeal and genital diseases, related skin and respiratory infections, varicella-zoster, chicken pox, herpes zoster, post-herpetic neuralgia, conjunctivitis, keratoconjunctivitis, keratitis. |
| HHV | Exanthem subitum, infectious mononucleosis. |
| EBV | Infectious mononucleosis, chronic fatigue syndrome, lymphoma, |

TABLE IV-continued

Examples of viral infections and related pathologies treatable with compounds described in this invention

| Virus | Viral infection/cancer or other virus-associated pathology |
| --- | --- |
| | conjunctivitis, keratitis, and related infections of the eye. |
| Adenoviruses | Upper and lower respiratory tract infections, pneumonia, conjunctivitis. |
| RSV | Upper and lower respiratory tract infections, pneumoma. |
| PMV | Mumps and related manifestations, e.g., conjunctivitis. |
| MV, RV | Measles, Rubella ("German measles") and related manifestations. |
| Coxsackie viruses | Conjunctivitis, diabetes mellitus, respiratory infections. |
| Influenza viruses | Upper and lower respiratory tract infections, pneumoma. |

HIV, Human Immunodeficiency Virus; HTLV, Human T-cell Lymphocyte Virus; HPV, Human Papilloma Virus; HAV, Hepatitis A Virus; HBV, Hepatitis B Virus; HAV, Hepatitis C Virus; CMV, Cytomegalovirus; HSV, Herpes Simplex Virus (Types I & II); HHV, Human Herpes Virus; EBV, Epstein-Barr Virus; RSV, Respiratory Syncytial Virus; VZV, Varicella-Zoster Virus; PMV, Paramyxovirus; MV, Measles (Rubeola) Virus; RV, Rubella Virus

TABLE V

HIV related infections and diseases treatable with compounds described in this invention

| Organ system | Viral infection/manifestation or other HIV-associated disease |
| --- | --- |
| Immunologic | AIDS, primary HIV infection. |
| Dermatological | Anogenital cancers including rectal and cervical cancer, Kaposi's sarcoma, squamous cell carcinoma, hairy leukoplakia, molluscum contagiosum, warts (HPV infections), seborrheic dermatitis, psoriasis, xeroderma, HSV and varicella-zoster infections. |
| Hematologic | Non-Hodgkin's lymphoma, B cell lymphoma, anemia, neutropenia, thrombocytopenia. |
| Gastrointestinal | Anorexia, gastroparesis, diarrhea, malabsorption, gastrointestinal CMV infections, esophagitis, colitis, hepatitis, lymphoma. |
| Ocular | Conjunctivitis, keratitis, keratoconjunctivitis, uveitis, retinitis, chorioretinitis, CMV retinitis, iridocyclitis, vitreitis, choroiditis, papilledema, Kaposi's sarcoma, lymphoma, ocular palsies, conjunctival warts, pre-neoplastic and neoplastic diseases of the eye. |
| Cardiac | Myocarditis, endocarditis, pericarditis. |
| Pulmonary | CMV pneumonitis, lymphoid interstitial pneumonitis. |
| Nephrologic | HIV nephropathy, renal cell carcinoma, amyloidosis, uropathy. |
| Rheumatologic | Arthralgia, fibromyalgia, Reiter's syndrome, psoriatic arthritis, vasculitis. |
| Neurologic | Dementia, viral meningitis, viral encephalitis, HIV encephalopathy, progressive multifocal leukoencephalopathy, CNS lymphoma, peripheral and autonomic neuropathies. |
| Psychiatric | Dysphoric mood disorders, depression, depression associated with chronic diseases and medications, bipolar disorder, anxiety disorders, chronic fatigue syndrome, chronic pain, psychoses, substance abuse disorders and drug addiction. |
| General | Lymphoma, metastatic lymphoma, Kaposi's sarcoma, wasting syndrome. |

TABLE VI

Examples of neurological and psychiatric disorders that can be treated with compounds described in this invention Neurological Disorders Migraine headaches
Alzheimer's disease
Parkinson's disease
Pain disorders including algesia, hyperalgesia, acute and chronic pain, allodynia
Chronic fatigue syndrome
Amnesia

TABLE VI-continued

Examples of neurological and psychiatric disorders that can be treated with compounds described in this invention Psychiatric Disorders Dysphoric mood disorders
Dysthymic disorder
Depression including depression associated with
chronic diseases and medications
Manic depressive disorder
Anxiety states including panic disorder and agoraphobia
Post menstrual syndrome
Obsessive-compulsive disorder, schizophrenia, chronic fatigue syndrome
Substance abuse and drug addiction

TABLE VII

Diseases of the eye treatable with compounds described in this invention
1. Diseases caused by viruses or associated with viral infections Disease Virus

| | |
|---|---|
| Blepharitis | HSV, VZV, Vaccinia, HPV, molluscum contagiosum |
| Conjunctivitis | HSV, VZV, EBV, Adenovirus, Vaccinia, Variola, HPV, molluscum contagiosum, influenza |
| Follicular c. | Newcastle, measles, mumps, rubella, molluscum contagiosum |
| Hemorrhagic c. | Enterovirus, coxsackie |
| Catarrhal c | Rubella |
| Keratitis | HSV, VZV, EBV, Adenovirus, Vaccinia, Variola, HPV, molluscum contagiosum |
| Keratoconjunctivitis | HSV, VZV, EBV, Adenovirus, Vaccinia, Variola, HPV, molluscum contagiosum |
| Retinitis | CMV |
| Uveitis | HPV |
| Conjunctival warts | HPV |
| C. epithelial neoplasms | HPV |

2. Ocularplastic diseases
   Benign tumors: Keratocanthoma, molluscum contagiosum, dermoid cysts, neurofibroma, neurofibromatosis, schwannoma (neurilemoma), pleiomorphic adenoma
   Malignant tumors: Basal cell carcinoma, squamous cell carcinoma, mucoepidermoid carcinoma, melanoma, retinoblastoma, embryonal rhabdomyosarcoma, meningioma, adenoid cystic carcinoma, lymphoid tumors of the orbit, mesenchymal tumors (fibrous hystiocytoma) of the orbit, nasopharyngeal carcinoma
   Vascular lesions: Hemangioma, lymphangioma.
3. Inflammatory/immunological ocular diseases
   Acute allergic conjunctivitis and hypersensitivity reactions
   Drug-related inflammation and hypersensitivity reactions
   Chronic (vernal) conjunctivitis
   Contact lens-associated conjunctivitis, e.g. giant papillary conjunctivitis
   Cojunctival ulceration, including ulceration associated with mucous membrane pemphigoid and the Steven's-Johnson syndrome, leading to progressive fibrosis and scarring, cicatrization and symblepharon.
   Corneal abrasion, corneal ulceration, or corneal injury of any etiology.
4. Other lesions
   Retina: Macular degeneration, retinopathy, including diabetic r. and hypertensive r.
   Lens: Cataract, all etiologies including rheumatological and collagen vascular diseases
   Uvea: Ueitis, vitreitis, all etiologies, including UV radiation and diabetes.

All publications, patents and patent applications mentioned in this specification are herein incorporated by reference into the specification in their entirety for all purposes.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A compound of the formula

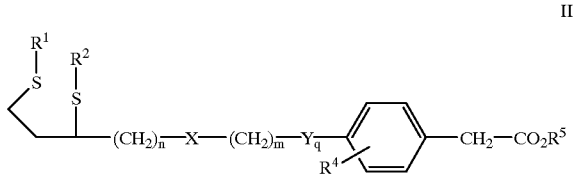

wherein:
$R^1$ is hydrogen;
$R^2$ is hydrogen; or $R^1$ and $R^2$ together with the sulfurs to which they are bound join to form a 1,2-dithiolane ring;
X is a member selected from the group consisting of O, NR, C(O)O, OC(O)O and C(O)NR, wherein R is a member selected from the group consisting of hydrogen, optionally substituted $(C_1-C_6)$alkyl and optionally substituted aryl;
Y is a member selected from the group consisting of O, S and $NR^3$, wherein $R^3$ is a member selected from the group consisting of hydrogen and optionally substituted $(C_1-C_6)$alkyl;
$R^4$ is a member selected from the group consisting of hydrogen, halogen, optionally substituted $(C_1-C_6)$alkyl and optionally substituted $(C_1-C_6)$alkoxy;
$R^5$ is a member selected from the group consisting of hydrogen and optionally substituted $(C_1-C_6)$alkyl;
n is an integer from 2 to 14;
m is an integer from 0 to 14; and
q is an integer from 0 to 1, with the proviso that when m is 0 then q is 0.

2. A compound in accordance with claim 1, wherein:
m is an integer from 1 to 6;
q is 1; and
$R^4$ is hydrogen.

3. A compound in accordance with claim 2, wherein:
$R^1$ and $R^2$ join to form a 1,2-dithiolane ring;
X is C(O)NR, wherein R is a member selected from the group consisting of hydrogen and optionally substituted $(C_1-C_6)$alkyl;
Y is O;
n is 4; and
m is 2.

4. A compound in accordance with claim 3, wherein:
R is methyl.

5. A compound in accordance with claim 2, wherein:
$R^1$ is hydrogen;
$R^2$ is hydrogen;
X is C(O)NR, wherein R is a member selected from the group consisting of hydrogen and optionally substituted $(C_1-C_6)$alkyl;

y is O;
n is 4;
m is 2; and
R⁵ is hydrogen.

6. A compound in accordance with claim 5, wherein:
R is methyl.

7. A compound in accordance with claim 2, wherein:
R¹ and R² join to form a 1,2-dithiolane ring;
X is C(O)O
y is O;
n is 4; and
m is 2.

8. A compound in accordance with claim 2, wherein:
R¹ is hydrogen;
R² is hydrogen;
X is C(O)O;
y is O;
n is 4; and
m is 2.

9. A compound in accordance with claim 2, wherein:
R¹ and R² join to form a 1,2-dithiolane ring;
x is O;
y is O;
n is 5; and
m is 2.

10. A compound in accordance with claim 2, wherein:
R¹ is hydrogen;
R² is hydrogen;
x is O;
y is O;
n is 5; and
m is 2.

11. A compound in accordance with claim 2, wherein:
R¹ and R² join to form a 1,2-dithiolane ring;
X is OC(O)O;
Y is O;
n is 4; and
m is 2.

12. A compound in accordance with claim 2, wherein:
R¹ is hydrogen;
R² is hydrogen;
X is OC(O)O;
Y is O;
n is 4; and
m is 2.

13. A compound in accordance with claim 1, wherein:
m is 0;
q is 0; and
R⁵ is hydrogen.

14. A compound in accordance with claim 13, wherein:
R¹ and R² join to form a 1,2 dithiolane ring;
X is C(O)NR, wherein R is a member selected from the group consisting of hydrogen and optionally substituted ($C_1$–$C_6$)alkyl; and
n is 4.

15. A compound in accordance with claim 14, wherein:
R is methyl.

16. A compound in accordance with claim 13, wherein:
R¹ is hydrogen;
R² is hydrogen;
X is C(O)NR, wherein R is a member selected from the group consisting of hydrogen and optionally substituted ($C_1$–$C_6$)alkyl; and
n is 4.

17. A compound in accordance with claim 16, wherein:
R is methyl.

18. A compound in accordance with claim 13, wherein:
R¹ and R² join to form a 1,2-dithiolane ring;
X is O; and
n is 5.

19. A compound in accordance with claim 13, wherein:
R¹ is hydrogen;
R² is hydrogen;
X is O; and
n is 5.

20. A compound in accordance with claim 1, wherein:
m is an integer from 2 to 14;
q is 0; and
R⁵ is hydrogen.

21. A compound in accordance with claim 20, wherein:
R¹ and R² join to form a 1,2-dithiolane ring;
X is C(O)NR, wherein R is a member selected from the group consisting of hydrogen and optionally substituted ($C_1$–$C_6$)alkyl;
n is 4; and
m is 3.

22. A compound in accordance with claim 21, wherein:
R is methyl.

23. A compound in accordance with claim 20, wherein:
R¹ and R² join to form a 1,2 dithiolane ring;
X is O;
n is 5; and
m is 3.

24. A compound in accordance with claim 20, wherein:
R¹ is hydrogen;
R² is hydrogen;
X is O;
n is 5; and
m is 3.

25. A compound in accordance with claim 2 wherein said 1,2 dithiolane ring is the R form.

26. A pharmaceutical composition comprising a compound of the formula compound of the formula

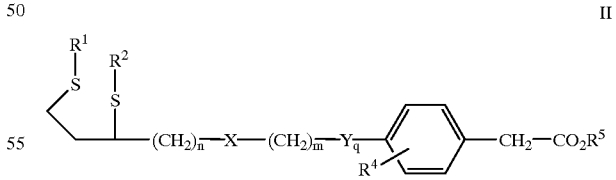

II wherein:
R¹ is hydrogen;
R² is hydrogen; or R¹ and R² together with the sulfurs to which they are bound join to form a 1,2-dithiolane ring;
X is a member selected from the group consisting of O, NR, C(O)O, OC(O)O and C(O)NR, wherein R is a member selected from the group consisting of hydrogen, optionally substituted ($C_1$–$C_6$)alkyl and optionally substituted aryl;

Y is a member selected from the group consisting of O, S and $NR^3$, wherein $R^3$ is a member selected from the group consisting of hydrogen and optionally substituted $(C_1-C_6)$alkyl;

$R^4$ is a member selected from the group consisting of hydrogen, halogen, optionally substituted $(C_1-C_6)$alkyl and optionally substituted $(C_1-C_6)$alkoxy;

$R^5$ is a member selected from the group consisting of hydrogen and optionally substituted $(C_1-C_6)$alkyl;

n is an integer from 2 to 14;

m is an integer from 0 to 14; and q is an integer from 0 to 1, with the proviso that when m is 0 then q is 0; or a pharmaceutical acceptable salt or solvate thereof; and a pharmaceutical acceptable carrier.

27. A composition in accordance with claim 26, wherein:

m is an integer from 1 to 6;

q is 1; and $R^5$ is hydrogen.

28. A composition in accordance with claim 26, wherein:

m is 0;

q is 0; and $R^5$ is hydrogen.

29. A composition in accordance with claim 26, wherein:

m is an integer from 2 to 14;

q is 0; and $R^5$ is $(C_1-C_6)$alkyl.

30. A method of treating a PPARγ mediated disease, said method comprising administering to a subject a therapeutically effective amount of a compound of the of the formula

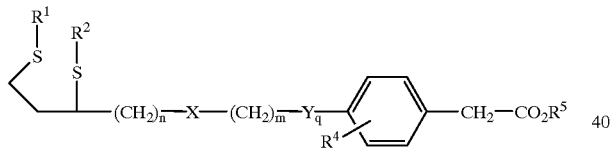

II wherein:

$R^1$ is hydrogen;

$R^2$ is hydrogen; or $R^1$ and $R^2$ together with the sulfurs to which they are bound join to form a 1,2-dithiolane ring;

X is a member selected from the group consisting of O, NR, C(O)O, OC(O)O and C(O)NR, wherein R is a member selected from the group consisting of hydrogen, optionally substituted $(C_1-C_6)$alkyl and optionally substituted aryl;

Y is a member selected from the group consisting of O, S and $NR^3$, wherein $R^3$ is a member selected from the group consisting of hydrogen and optionally substituted $(C_1-C_6)$alkyl;

$R^4$ is a member selected from the group consisting of hydrogen, halogen, optionally substituted $(C_1-C_6)$alkyl and optionally substituted $(C_1-C_6)$alkoxy;

$R^5$ is a member selected from the group consisting of hydrogen and optionally substituted $(C_1-C_6)$alkyl;

n is an integer from 2 to 14;

m is an integer from 0 to 14; and q is an integer from 0 to 1, with the proviso that when m is 0 then q is 0.

31. A method in accordance with claim 30, wherein:

m is an integer from 1 to 6;

q is 1; and $R^5$ is hydrogen.

32. A method in accordance with claim 30, wherein:

m is 0;

q is 0; and $R^5$ is hydrogen.

33. A method in accordance with claim 30, wherein:

m is an integer from 2 to 14;

q is 0, and $R^5$ is hydrogen.

* * * * *